US012674141B2

(12) United States Patent
Shyu et al.

(10) Patent No.: US 12,674,141 B2
(45) Date of Patent: Jul. 7, 2026

(54) GENE-ENGINEERED MESENCHYMAL STEM CELLS AND APPLICATIONS THEREOF

(71) Applicant: CHINA MEDICAL UNIVERSITY, Taichung (TW)

(72) Inventors: Woei-Cherng Shyu, Taichung (TW); Chien-Lin Chen, Taichung (TW); Yi-Hui Lee, Taichung (TW); Long-Bin Jeng, Taichung (TW); Chang-Hai Tsai, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 1079 days.

(21) Appl. No.: 17/756,247

(22) PCT Filed: Sep. 27, 2020

(86) PCT No.: PCT/CN2020/118008
§ 371 (c)(1),
(2) Date: May 19, 2022

(87) PCT Pub. No.: WO2021/057942
PCT Pub. Date: Apr. 1, 2021

(65) Prior Publication Data
US 2023/0220350 A1     Jul. 13, 2023

Related U.S. Application Data

(60) Provisional application No. 62/907,338, filed on Sep. 27, 2019.

(51) Int. Cl.
| | |
|---|---|
| *C12N 5/0775* | (2010.01) |
| *A61K 9/00* | (2006.01) |
| *A61K 35/28* | (2015.01) |
| *A61P 9/10* | (2006.01) |
| *C12N 15/86* | (2006.01) |

(52) U.S. Cl.
CPC .......... *C12N 5/0663* (2013.01); *A61K 9/0019* (2013.01); *A61K 35/28* (2013.01); *A61P 9/10* (2018.01); *C12N 15/86* (2013.01); *C12N 2740/16043* (2013.01)

(58) Field of Classification Search
CPC ... C12N 5/0663; C12N 5/0665; C12N 5/0668
See application file for complete search history.

(56) References Cited

U.S. PATENT DOCUMENTS

| | | |
|---|---|---|
| 2004/0258669 A1 | 12/2004 | Dzau et al. |
| 2006/0211600 A1 | 9/2006 | Dzau et al. |
| 2012/0121611 A1 | 5/2012 | Lodie et al. |
| 2019/0038717 A1 | 2/2019 | Sung et al. |

FOREIGN PATENT DOCUMENTS

| | | |
|---|---|---|
| CN | 102764272 A | 11/2012 |
| CN | 109477119 A | 3/2019 |

OTHER PUBLICATIONS

Gharibi, Borzo, et al. "Inhibition of Akt/mTOR attenuates age-related changes in mesenchymal stem cells." Stem cells 32.8 (2014): 2256-2266. (Year: 2014).*
Bárcia, R. N., et al. "What makes umbilical cord tissue-derived mesenchymal stromal cells superior immunomodulators when compared to bone marrow derived mesenchymal stromal cells?." Stem cells international 2015.1 (2015): 583984. (Year: 2015).*
Zuidema, Mozow Y., and Cuihua Zhang. "Ischemia/reperfusion injury: The role of immune cells." World journal of cardiology 2.10 (2010): 325. (Year: 2010).*
Office Action and Search Report issued for the corresponding Taiwan application No. 109133682 with English translation of Search Report.
Cosette M. Rivera-Cruz et al: "The Immunomodulatory Effects of Mesenchymal Stem Cell Polarization within the Tumor Microenvironment Niche", Stem Cells International, vol. 2017, Jan. 1, 2017 (Jan. 1, 2017), pp. 1-17, XP055540732, ISSN: 1687-966X, DOI: 10.1155/2017/4015039.
Davies et al., "Mesenchymal Stromal Cell Secretion of Programmed Death-1 Ligands Regulates T Cell Mediated Immunosuppression" Stem Cells 2017;35:766-776.
Extended European search report (EESR) issued for the corresponding European application No. 20869084.2.
F. van den Akker et al., "Mesenchymal Stem Cell Therapy for Cardiac Inflammation: Immunomodulatory Properties and the Influence of Toll-Like Receptors" Mediators of Inflammation 31, vol. 2013, pp. 1-13.
Form PCT/ISA/210 (International Search Report) issued for the corresponding PCT application No. PCT/CN2020/118008.
Form PCT/ISA/237 (Written Opinion) issued for the corresponding PCT application No. PCT/CN2020/118008.
Francisco et al., "PD-L1 regulates the development, maintenance, and function of induced regulatory T cells" J Exp Med 2009; 206:3015-3029.
International Preliminary Report on Patentability issued for the corresponding PCT application No. PCT/CN2020/118008.
Ki-Jong Rhee et al: Cell-Mediated Effects of Tumor Support or Suppression, International Journal of Molecular Sciences, vol. 16, No. 12, Dec. 16, 2015 (Dec. 16, 2015), pp. 30015-30033, XP055601382, DOI: 10.3390/ijmsl61226215.

(Continued)

*Primary Examiner* — Robert J Yamasaki
(74) *Attorney, Agent, or Firm* — Prosyla Group, PC

(57) ABSTRACT

Accordingly, the present disclosure provides a population of genetically engineered mesenchymal stem cells (MSCs), comprising an expression vector comprising an Akt or HGF gene and a PD-L1 gene. Also provided is a method for synergistically increasing survival status and immunomodulatory ability of an MSC or enhancing proliferation of an MSC, comprising transfecting an MSC with an Akt or HGF gene and a PD-L1 gene and a method for preventing, ameliorating and/or treating an ischemia condition, enhancing neuroregeneration or reducing neuronal death, comprising administering an effective amount of a population of genetically engineered MSCs of the present disclosure to a subject in need thereof.

19 Claims, 36 Drawing Sheets

(56)                    References Cited

OTHER PUBLICATIONS

Li et al., "A naturally occurring CD8+CD122+ T-cell subset as a memory-like Treg family" Cellular & molecular immunology, vol. 11, May 5, 2014, pp. 326-331.

Li, H et al., "Immunomodulatory Functions of Mesenchymal Stem Cells in Tissue Engineering" Stem Cells International vol. 2019, Article ID 9671206, 18 pages.

Liang, X.H: "Effect of mesenchymal stem cells on immune cells in cardiac inflammation after myocardial infarction and its mechanism", Medical Journal of National Defending Forces in Southwest China, vol. 24, No. 10, Oct. 31, 2014 (Oct. 31, 2014), pp. 1149-1152, XP009526958, ISSN: 1004-0188, DOI: 10.3969/j.issn.1004-0188.2014.10.047.

Liu et al., "Human umbilical cord mesenchymal stem cells infected with adenovirus expressing HGF promote regeneration of damaged neuron cells in a Parkinson's disease model" BioMed research international, vol. 2014, Sep. 3, 2014, Article: 909657.

Reenam et al., "A Comparison of Phenotypic and Functional Properties of Mesenchymal Stromal Cells and Multipotent Adult Progenitor Cells" Frontiers in Immunology, vol. 10, Jan. 1, 2019 (Jan. 1, 2019), XP055643204, DOI: 10.3389/fimmu.2019.01952.

Shake et al., "Mesenchymal Stem Cell Implantation in a Swine Myocardial Infarct Model: Engraftment and Functional Effects" Ann Thorac Surg 2003;73:1919-1926.

Shi Yufang et al: "Immunoregulatory mechanisms of mesenchymal stem and stromal cells in inflammatory diseases", Nature Reviews. Nephrology, Nature Publishing Group, GB, vol. 14, No. 8, Jun. 12, 2018 (Jun. 12, 2018), pp. 493-507, XP036544389, ISSN: 1759-5061, DOI: 10.1038/S41581-018-0023-5.

Tanaka et al., "Hypoxic preconditioning of human cardiosphere-derived cell sheets enhances cellular functions via activation of the PI3K/Akt/mTOR/HIF-1α pathway"Am J Transl Res. 2017; 9: 664-673.

Toma et al., "Human Mesenchymal Stem Cells Differentiate to a Cardiomyocyte Phenotype in the Adult Murine Heart" Circulation 2002;105:93-98.

Zhao, Liyan et al. "Enhanced cell survival and paracrine effects of mesenchymal stem cells overexpressing hepatocyte growth factor promote cardioprotection in myocardial infarction" Experimental cell research, vol. 344, Mar. 26, 2016, pp. 30-39.

Office Action with Search Report issued on Jul. 8, 2025 for corresponding P.R.C. (China) Patent Application No. 202080067799X (with English translation to search report attached).

* cited by examiner

Akt p-Akt

ERK p-ERK

β-actin

GENE-ENGINEERED MESENCHYMAL STEM CELLS AND APPLICATIONS THEREOF

FIELD OF THE INVENTION

The present invention relates to a field of engineered stem cells and its applications. Particularly, the engineered stem cells comprise at least a survival gene and an immune checkpoint gene and can be used to treat or ameliorate ischemia conditions, to enhance neuroregeneration, or to reduce neuronal death.

BACKGROUND OF THE INVENTION

Stroke and acute myocardial ischemia (AMI) are both leading causes of death and disability in the world. Although recombinant tissue plasminogen activator (rt-PA) is a well-established and widely used treatment for acute ischemic stroke and acute myocardial ischemia, the narrow time window for administration limits the benefit of thrombolytic therapy. A novel treatment with a greatly improved efficacy or benefit is needed.

Mesenchymal stromal cells (MSCs) exert broad immunosuppressive potential and modulate the activity of cells of innate and adaptive immune systems, and have been regarded as a therapeutic option for the treatment of many diseases. However, understanding the behavior of MSCs remains elusive with respect to harnessing their capabilities to aid in treatment and related applications. Many therapies involving MSCs have been tested but showed little efficacy.

Therefore, methods to improve their survival are much needed for the therapeutic application of MSCs.

SUMMARY OF THE INVENTION

The present disclosure is based on genetically engineered mesenchymal stem cells (MSCs) that express elevated levels of Akt or hepatocyte growth factor (HGF) and PD-L1 and methods of using the MSCs to treat and ameliorate ischemia conditions, enhance neuroregeneration or reduce neuronal death. The MSCs and methods of the present disclosure result in significant and unexpected improvement in recovery and repair of injuries in subjects in need of treatment.

In one aspect, the present disclosure provides a method for preventing, ameliorating and/or treating ischemia condition, enhancing neuroregeneration or reducing neuronal death in a subject, comprising administering an effective amount of a population of mesenchymal stem cells comprising survival genes (ex. Akt or HGF) and immune checkpoint genes (ex. PD-L1) to the subject. Also provided is a use of a population of mesenchymal stem cells comprising survival genes (ex. Akt or HGF) and immune check-point genes (ex. PD-L1) in the manufacture of a medicament for treating or ameliorating ischemia conditions in a subject. In one embodiment, the mesenchymal stem cells are genetically engineered.

Examples of the ischemia conditions include, but are not limited to, stroke and myocardial infarction (MI). In one embodiment, the MI is acute myocardial infarction (AMI). In one embodiment, the administration of the present disclosure attenuates the MI-Induced fibrosis. In another embodiment, the administration of the present disclosure also reduces inflammation on ischemic tissue. In another embodiment, the administration of the present disclosure attenuates post-MI LV dysfunction and reduces infarct size after MI. In another embodiment, the administration of the present disclosure increases the expression of regulatory molecules on T cells in spleens after stroke, reduces neuronal death from stroke brain damage and/or reduces inflammatory responses, but enhances accumulation of CD8+ CD122+ Tregs in the ischemic brain.

In one embodiment, the administration reduces inflammatory response but enhances accumulation of $CD8^+$ $CD122^+$ Tregs in an ischemic tissue. Preferably, the ischemic tissue is ischemic brain tissue.

In one embodiment, the administration increases the expression of regulatory molecules in T cells in the subject.

In one embodiment, the effective amount of the population of genetically engineered MSCs of the present disclosure elevates expression of Akt or HGF and PD-L1.

Certain embodiments of the effective amount of the population of genetically engineered MSCs of the present disclosure are those ranging from about $1 \times 10^5$ cells to about $1 \times 10^8$ cells. In some embodiments, the effective amount of the population of genetically engineered MSCs ranges from about $3 \times 10^5$ cells to about $3 \times 10^8$ cells, about $5 \times 10^5$ cells to about $5 \times 10^8$ cells, about $7 \times 10^5$ cells to about $7 \times 10^8$ cells, about $1 \times 10^6$ cells to about $1 \times 10^8$ cells, about $3 \times 10^6$ cells to about $3 \times 10^8$ cells, about $5 \times 10^6$ cells to about $5 \times 10^8$ cells, about $7 \times 10^6$ cells to about $7 \times 10^8$ cells, about $1 \times 10^7$ cells to about $1 \times 10^8$ cells, about $3 \times 10^7$ cells to about $3 \times 10^8$ cells, about $5 \times 10^7$ cells to about $5 \times 10^8$ cells, about $7 \times 10^7$ cells to about $7 \times 10^8$ cells, about $1 \times 10^5$ cells to about $1 \times 10^6$ cells, about $3 \times 10^5$ cells to about $3 \times 10^6$ cells, about $5 \times 10^5$ cells to about $5 \times 10^6$ cells or about $7 \times 10^5$ cells to about $7 \times 10^6$ cells.

In some embodiments, the administration includes, but is not limited to, intravenous injection, intracarotid injection, intraarterial injection, or a combination thereof. A certain embodiment of the administration is intracarotid injection in combination with intravenous injection. Another certain embodiment of the administration is intraarterial injection in combination with intravenous injection. Preferably, the intravenous injection is performed before the intraarterial injection. In a particular embodiment, the administration is intracarotid injection in combination with intravenous injection or intraarterial injection in combination with intravenous injection in a subject suffering from stroke or AMI. In a further particular embodiment, the administration is in an effective amount ranging from about $1 \times 10^4$ cells to about $1 \times 10^6$ cells, preferably from about $5 \times 10^4$ cells to about $5 \times 10^5$ cells, for intracarotid injection and about $3 \times 10^4$ cells to about $1 \times 10^7$ cells, preferably from about $1 \times 10^5$ cells to about $5 \times 10^6$ cells, for intravenous injection.

In another aspect, the present disclosure provides a method for synergistically increasing survival status and immunomodulatory ability of an MSC or enhancing proliferation of an MSC, comprising transfecting an MSC with an Akt or HGF gene and a PD-L1 gene.

In one aspect, the present disclosure provides a population of genetically engineered mesenchymal stem cells (MSCs), wherein the MSCs comprising a survival gene (ex. Akt or HGF) and an immune check-point gene (ex. PD-L1). In one embodiment, the mesenchymal stem cells are genetically engineered.

In one embodiment, the mesenchymal stem cells described herein are selected from the group consisting of umbilical cord mesenchymal stem cells (UMSCs), adipose derived mesenchymal stem cells (ADSCs), and bone marrow mesenchymal stem cells (BMSCs).

In one embodiment, the programmed death-ligand 1 or Akt or HGF described herein is transduced with a transposon or a vector. In some embodiments, the survival gene (ex. Akt or HGF) and immune check-point gene (ex. PD-L1) are comprised in an expression vector. In one embodiment, the expression vector is a viral vector. In a certain embodiment, the viral vector is a lentiviral vector.

In another aspect, the present disclosure provides a pharmaceutical composition comprising the population of genetically engineered MSCs of the present disclosure.

BRIEF DESCRIPTION OF THE DRAWINGS

FIG. 6D-1 shows the gating strategy of IA-IV-UMSC-PD-L1-Akt for analyzing inflammatory cells in the cerebral hemisphere by flow cytometry.

FIG. 6D-2 shows the results of flow cytometry analysis of $CD8^+$, $CD8^+CD122^+$, $CD8^+CD122^+IL-10^+$ and $CD19^+IL-10^+$ cells in the cerebral hemisphere after IA-IV-UMSC-PD-L1-Akt treatment.

FIGS. 7A-1 to 7A-3 show the gating strategy of spleen cells treated with UMSC-PD-L1-Akt and analyzed by flow cytometry.

FIG. 7A-4 shows the results of flow cytometry analysis of $CD11b^+PD-L1^+$, $CD11c^+PD-L1^+$, $CD19^+PD-L1^+$, $CD4^+PD-L1^+$ and $CD8^+PD-L1^+$ cells of spleen cells treated with UMSC-PD-L1-Akt.

DETAILED DESCRIPTION OF THE INVENTION

Figure 1A:
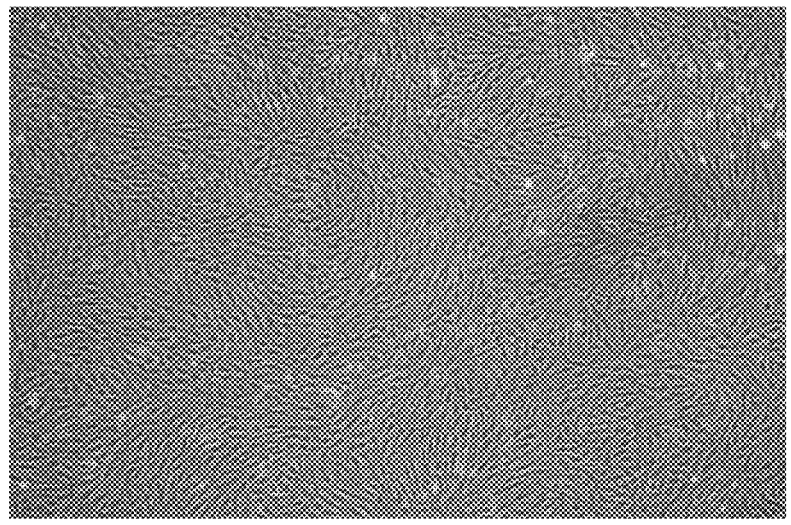
FIG. 1A shows the results of the observation of primary cultures of umbilical cord mesenchymal stem cells.

Unless defined otherwise, all scientific or technical terms used herein have the same meaning as those understood by persons of ordinary skill in the art to which the present invention belongs. Any method and material similar or equivalent to those described herein can be understood and used by those of ordinary skill in the art to practice the present invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims of the present invention are approximate and can vary depending upon the desired properties sought by the present invention.

The term "a/an" should mean one or more than one of the objects described in the present invention. The term "and/or" means either one or both of the alternatives. The term "a cell" or "the cell" may include a plurality of cells.

The term "and/or" is used to refer to both things or either one of the two mentioned.

The term "in vivo" generally means inside a living organism. The term "ex vivo" generally means outside of a living organism, such as an experiment taking place at an artificial environment created outside of the organism.

The term "genetically engineered" or "genetic engineering" of cells means manipulating genes using genetic materials for the change of gene copies and/or gene expression level in the cell. The genetic materials can be in the form of DNA or RNA. The genetic materials can be transferred into cells by various means including viral transduction and non-viral transfection. After being genetically engineered, the expression level of certain genes in the cells can be altered permanently or temporarily.

The term "transduction" or "transduce" means using a virus to deliver the genetic material into cells, wherein the virus can be an integrating or non-integrating virus. The integrating virus used in the present invention can be lentivirus or retrovirus. The integrating virus allows integration of its encoding genes into the transduced cells that are infected with the viral particles. The non-integrating virus can be adenovirus or Sendai virus. Non-viral methods may also be used in the present disclosure such as by transfecting DNA or RNA materials into cells. The DNA materials can be in the form of PiggyBac, minicircle vectors, or episomal plasmids. The RNA material may be in the form of mRNA or miRNA.

The term "expression vector" means the agent carrying foreign genes into cells for expression without degradation. The expression vector in the present invention can be plasmid, viral vectors, and artificial chromosomes.

The term "elevated expression" herein means the increased expression of RNA or protein of the genes of interest in genetically engineered cells, when compared to the expression level of those genes in the non-engineered cell counterpart.

The term "purification" of cells herein means to use properties that are unique to the particular cell of interest to isolate and obtain the cell of interest. In some embodiments, the unique properties are the presence or absence of the protein on the cell surface, referred to as "surface marker" herein. In some embodiments, "positive markers" mean the surface markers that are present or expressed on the cell of interest. In some embodiments, "negative markers" mean the surface markers that are absent from the cell of interest.

The terms "treatment," "treating," and "treat" generally refer to obtaining a desired pharmacological and/or physiological effect. The effect maybe preventive in terms of completely or partially preventing a disease, disorder, or symptom thereof, and may be therapeutic in terms of a partial or complete cure for a disease, disorder, and/or symptoms attributed thereto. "Treatment" used herein covers any treatment of a disease in a mammal, preferably a human, and includes (1) suppressing development of a disease, disorder, or symptom thereof in a subject or (2) relieving or ameliorating the disease, disorder, or symptom thereof in a subject.

The terms "individual," "subject," and "patient" herein are used interchangeably and refer to any mammalian subject for whom diagnosis, treatment, or therapy is desired.

The term "effective amount" refers to the amount of cells or their derived progenies that, when administered to a patient or a subject in need for treating a disease or disorder, is sufficient to have a beneficial effect with respect to that disease or disorder. The therapeutically effective amount will vary depending on the conditions of the disease or disorder and its severity. It is not limited to the range stated in the specification. Determining the therapeutically effective amount of given cells or their derived progeny is within the ordinary skill of the art and requires no more than routine experimentation.

The term "pharmaceutical composition" of this invention includes an effective amount of live cells to treat a degenerative condition. The cell component may be a mixture of culture cells or an isolated population of cells, such as differentiated tissue cells, progenitor cells, and/or stem cells. The pharmaceutical composition of this invention is in liquid form or cell suspension buffer, and it may contain pharmaceutically acceptable excipients that stabilize the liquid suspension and help cell viability.

The term "ischemia conditions" in this invention refers to conditions resulting from or accompanied by ischemic diseases (or "ischemia diseases"), which are usually characterized as reduced blood flow to a tissue or organ due to undesirable vascular conditions, such as blood vessel stenosis or aneurysm rupture. Myocardial infarction (MI), ischemic stroke, and critical limb ischemia are the three most common ischemic diseases. In some embodiments, the ischemia conditions comprise acute myocardial infarction (AMI) and ischemic stroke. In one embodiment, the ischemia condition is caused by AMI. In another embodiment, the ischemia condition is caused by ischemic stroke.

The term "PD-L1" refers to programmed death-ligand 1, the 40 kDa type 1 transmembrane protein that is encoded by the CD274 gene. PD-L1 binds to its receptor, PD-1, found on activated T cells, B cells, and myeloid cells. PD-L1 is also known as "CD274," "B7 homolog 1," and "B7-H1."

Programmed death-ligand 1 (PD-L1), also known as duster of differentiation 274 (CD274) or B7 homolog 1 (B7-H1), is a protein that in humans is encoded by the CD274 gene. The binding of PD-L1 to its receptor PD-1 dampens T cell activation, decreases proliferation and cyto- toxicity, and induces apoptosis. PD-1 is expressed on the cell surface of activated T and B cells, PD-L1 expressed on MSCs interacts with the PD-1 to provide an inhibitory signal in regulating cellular activation and proliferation (*J Exp Med* 2009; 206:3015-3029). Moreover, MSCs are found to inhibit the proliferation and function of effector T cells through both directly contacting activated T cells and indirectly secreting soluble PD-L1 (*Stem Cells* 2017; 35:766-776). However, poor engraftment of MSCs has been observed when MSCs were transplanted to heat the infarcted heart, with little improvement of heart function (*Ann Thorac Surg* 2003; 73:1919-1926). Low viability of transplanted MSCs, which showed only 1% vital cells 4 days post implantation, was also found in the infarcted heart (*Circulation* 2002; 105:93- 98).

Protein kinase B (PKB), also known as Akt, is a serine/ threonine-specific protein kinase that plays a key role in multiple cellular processes such as glucose metabolism, apoptosis, cell proliferation, transcription and cell migration. Akt regulates cellular survival and metabolism by binding and regulating many downstream effectors, e.g., Nuclear Factor-κB, Bcl-2 family proteins, master lysosomal regula- tor TFEB and murine double minute 2 (MDM2). Akt can promote growth factor-mediated cell survival both directly and indirectly. It has been found that hypoxic pre-condition- ing of transplanted cells, a brief incubation of cells before transplantation, protects human brain endothelium from ischemic apoptosis through activation of Akt-dependent pathways (Am J Transl Res. 2017; 9: 664-673). However, the Akt-MSCs still demonstrate room for improvement for repair and better recovery from ischemic injury.

The present disclosure surprisingly found that genetic modification of AU or HGF and PD-L1 in MSCs provides not only the survival signal but also an anti-inflammatory effect for robustly promoting improvement of the ischemic condition. The genetic modification described in the present disclosure can maintain and extend the survival status and immunomodulatory ability of the implanted MSCs in order to overcome the hypoxic environment of ischemic tissues and activated immune system with splenocytes.

Accordingly, the present disclosure provides a population of genetically engineered mesenchymal stem cells (MSCs), comprising an expression vector comprising survival genes (ex. Akt or HGF) and immune check-point genes (ex. PD-L1). Also provided is a method for synergistically increasing the survival status and immunomodulatory ability of an MSC or enhancing proliferation of an MSC, compris- ing transfecting an MSC with an Akt or HGF gene and a PD-L1 gene and a method for preventing, ameliorating and/or treating an ischemia condition, enhancing neurore- generation or reducing neuronal death, comprising admin- istering an effective amount of a population of genetically engineered MSCs of the present disclosure to a subject in need thereof.

The mesenchymal stem cells according to the disclosure can be obtained from different sources, preferably from umbilical cord, adipose tissue or bone marrow. According to different sources, the mesenchymal stem cells are umbilical cord mesenchymal stem cells (UMSCs), adipose derived mesenchymal stem cells (ADSCs), and bone marrow mes- enchymal stem cells (BMSCs). In some embodiments of this disclosure, MSCs are isolated and purified from the umbilical cord, and referred to as "umbilical MSC" or "UMSC." In some embodiments, it is established that the UMSC in this disclosure expresses the same selection of surface markers as the MSC isolated from other bodies, and demonstrates comparable activities.

The mesenchymal stem cells according to the disclosure are modified to express programmed death-ligand 1 and Akt or HGF. As used herein, the term "modified to express" in the present disclosure refers to transferring an exogenous gene or gene fragment into the mesenchymal stem cells so that they can express the exogenous gene or gene fragment. Preferably, this modification does not alter the differentia- tion potential of the mesenchymal stem cells, nor does it alter the immunomodulatory properties of the mesenchymal stem cells. In another aspect, this modification is preferred to be a stable modification, and the expression may be persistent or inducible. The mesenchymal stem cells accord- ing to the disclosure are modified to express programmed death-ligand 1 and Akt or HGF and still have pluripotent differentiation potential, such as, but not limited to, adipo- genesis, chondrogenesis, osteogenesis and vascularization, that is similar with the common mesenchymal stem cells without PD-L1 and Akt or HGF transductions.

The manners of modifying the mesenchymal stem cells with programmed cell death protein-1 and Akt or HGF are not limited. Preferably, the programmed death-ligand 1 or Akt or HGF is transduced with a transposon or lentivirus; more preferably, the transposon is piggyBac transposon. By applying piggyBac transposon, PD-L1 and Akt or HGF keep their expressions in 100-150 days. The results showed that piggyBac transposon can efficiently and stably transfect the bone marrow mesenchymal stem cells, and the gene modi- fication of piggyBac does not alter the DNA copy number and arrangement of the mesenchymal stem cells.

The genetically engineered mesenchymal stem cells (MSCs) of the present disclosure, comprises an expression vector comprising an Akt or HGF gene and a PD-L1 gene. In addition to the sequences of Akt or HGF and PD-L1, the vector of the present disclosure comprises one or more control sequences to regulate the expression of the poly- nucleotide of the pre sent disclosure. Manipulation of the isolated polynucleotide prior to its insertion into a vector may be desirable or necessary depending on the expression vector utilized. Techniques for modifying polynucleotides and nucleic acid sequences utilizing recombinant DNA methods are well known in the art. In some embodiments, the control sequences include, among others, promoters, leader sequences, polyadenylation sequences, propeptide sequences, signal peptide sequences, and transcription ter- minators. In some embodiments, suitable promoters are selected based on host cell selection.

A recombinant expression vector of the present disclosure is disclosed along with one or more expressions regulating regions such as a promoter and a terminator, a replication origin, etc., depending on the type of hosts into which they are to be introduced. Non-limiting examples of constitutive promoters include SFFV, CMV, PKG, MDNU3, SV40, Efla, UBC, and CAGG.

In some embodiments, the various nucleic acid and con- trol sequences described herein are joined together to pro- duce recombinant expression vectors which include one or more convenient restriction sites to allow for insertion or substitution of the polynucleotide of the present disclosure at such sites. Alternatively, in some embodiments, the poly- nucleotide of the present disclosure is expressed by inserting the polynucleotide or a nucleic acid construct comprising the sequence into an appropriate vector for expression. In some embodiments involving the creation of the expression vector, the coding sequence is located in the vector so that the coding sequence is operably linked with the appropriate control sequences for expression. The recombinant expression vector may be any suitable vector (e.g., a plasmid or virus) that can be conveniently subjected to recombinant DNA procedures and bring about the expression of the polynucleotide of the present disclosure. The choice of vector typically depends on the compatibility of the vector with the host cell into which the vector is to be introduced. The vector may be a linear or closed circular plasmid. In one embodiment, the vector is a viral vector. Examples of viral vectors include retroviral vectors, lentiviral vectors, adenovirus vectors, adeno-associated virus vectors, alphavirus vectors and the like. In a certain embodiment, the viral vector is a lentiviral vector. Lentiviral vectors are based on or derived from oncoretroviruses (the sub-group of retroviruses containing MLV), and lentiviruses (the sub-group of retroviruses containing HIV). Examples of such include, without limitation, human immunodeficiency virus (HIV), equine infectious anaemia virus (EIAV), simian immunodeficiency virus (SIV) and feline immunodeficiency virus (FIV). Alternatively, it is contemplated that other retroviruses can be used as a basis for a vector backbone such as murine leukemia virus (MLV).

In some embodiments, genetically engineered MSCs of the present disclosure have been tested in various differentiation assays to establish their comparability to the conventional MSC isolated from other locations of the mammalian body. The differentiation assays include adipogenic differentiation, osteogenic differentiation, and chondrogenic differentiation. In some embodiments, the differentiation assay further includes neuronal cell differentiation.

The population of genetically engineered MSCs of the present disclosure can synergistically increasing survival status and immunomodulatory ability of an MSC by transfecting an MSC with an Akt or HGF gene and a PD-L1 gene. Accordingly, the present disclosure provides a method for preventing, ameliorating and/or treating an ischemia condition, enhancing neuroregeneration or reducing neuronal death, comprising administering an effective amount of a population of genetically engineered MSCs of the present disclosure to a subject in need thereof.

In some embodiments, the ischemia condition includes, but is not limited to, stroke and myocardial infarction (MI). Preferably, the MI is acute myocardial infarction (AMI). The administration of the present disclosure attenuates the MI-Induced fibrosis. The administration of the present disclosure also reduces inflammation on ischemic tissue.

The administration increases the expression of regulatory molecules on T cells in the subject and reduces inflammatory response, but enhances accumulation of $CD8^+CD122^+$ Tregs in an ischemic tissue. The ischemic tissue treated with the population of genetically engineered MSCs of the present disclosure showed a significant increase in the total number of viable leukocytes including $CD3^+$ T cells, $CD4^+$ T cell, $CD11b^+PD-L1^+$ macrophage and $F4/80^+PD-L1^+$ microglia compared with the unaffected tissue, while the total cell numbers were unchanged between treatment and control groups in either tissue.

The effective amount of the population of genetically engineered MSCs of the present disclosure elevates expression of Akt or HGF and PD-L1. Particularly, the effective amount of the population of genetically engineered MSCs of the present disclosure ranges from about $1\times10^5$ cells to about $1\times10^8$ cells. Other embodiments of the amount are those described herein.

The mesenchymal stem cells according to the disclosure are contained in an injectable preparation. The injectable preparation may be prepared by publicly known methods. For example, the injectable preparations may be prepared, e.g., by dissolving, suspending or emulsifying the pharmaceutical composition in a sterile aqueous medium or an oily medium conventionally used for injections. Examples of the aqueous medium for injections include physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. Examples of the oily medium include sesame oil, soybean oil, etc., which may be used in combination with a solubilizing agent such as benzyl benzoate, benzyl alcohol, etc. The injection thus prepared is preferably filled in an appropriate ampoule.

Route of administration of MSC in this invention depends on the tissue or organs in need of treatment. In some embodiments with the subjects having myocardial infarction, the route of administering MSCs can be intravenous, intraarterial, or the combination thereof. Solutions containing the cells can be prepared in suitable diluents such as water, ethanol, glycerol, liquid polyethylene glycol(s), various oils, and/or mixtures thereof, and others known to those skilled in the art. In a certain embodiment, the administration is intracarotid injection in combination with intravenous injection in a subject suffering from a stroke or AMI. In a further particular embodiment, the administration is in an effective amount ranging from about $1\times10^5$ cells to about $3\times10^6$ for intracarotid injection and about $3\times10^5$ cells to about $3\times10^6$ for intravenous injection.

The administration according to the disclosure also comprises injecting the mesenchymal stem cells into a subject in need of such treatment through an intraarterial route in combination with an intravenous route. In one preferred embodiment of the disclosure, the intraarterial route is through the carotid artery.

In some embodiments of this invention, the process of administering MSCs is referred to by the terms "transplantation" or "implantation."

In one embodiment the engineered stem cell of the present disclosure can be administered with an additional active agent. In some embodiments, the engineered stem cell and the additional active agent can be administered concurrently, separately or simultaneously. In one embodiment, the engineered stem cell and the additional active agent can be administered periodically.

It is to be understood that if any prior art publication is referred to herein, such reference does not constitute an admission that the publication forms a part of the common general knowledge in the art.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

EXAMPLES

Methods and Materials:
Preparation, Isolation and Characterization of UMSCs, ADSCs or BMSCs The collected human umbilical cord tissues approved by the Institutional Review Board (IRB) of the China Medical University Hospital, Taichung were washed three times with $Ca^{2+}$ and $Mg^{2+}$-free PBS (DPBS, Life Technology). They were mechanically cut by scissors in a midline direction and the vessels of the umbilical artery, vein and outlining membrane were dissociated from the Wharton's jelly (WJ). The jelly content was then extensively cut into pieces smaller than 0.5 cm³, treated with collagenase type 1 (Sigma, St Louis, USA) and incubated for 3 h at 37° C. in a 95% air/5% $CO_2$ humidified atmosphere. The explants then were cultured in DMEM containing 10% fetal calf serum (FCS) and antibiotics at 37° C. in a 95% air/5% $CO_2$ humidified atmosphere. They were left undisturbed for 5-7 days to allow for migration of the cells from the explants. The cellular morphology of umbilical cord-derived mesenchymal stem cells (UMSCs) became homogenously spindle shaped in cultures after 4-8 passages, and the specific surface molecules of cells from the WJ were characterized by flow cytometric analysis. The cells were detached with 2 mM EDTA in PBS, washed with PBS containing 2% BSA and 0.1% sodium azide (Sigma, USA) and incubated with the respective antibody conjugated with fluorescein isothiocyanate (FITC) or phycoerythrin (PE) including CD13, CD29, CD44, CD73, CD90, CD105, CD166, CD49b, CD1q, CD3, CD10, CD14, CD31, CD34, CD45, CD49d, CD56, CD117, HLA-ABC, and HLA-DR (BD, PharMingen). Thereafter, the cells were analyzed using a Becton Dickinson flow cytometer (Becton Dickinson, San Jose, CA). The other MSCs including adipose mesenchymal stem cells (ADSCs) and bone marrow mesenchymal stem cells (BMSCs) were purchased from ATCC (ADSCs, PCS 500-011; BMSCs, PCS 500-012).

Plasmids Construction

Akt, HSF, PD-L1 and GFP cDNA from plasmids of Akt (0.1 µg) (pCMV6-myc-DDK-Akt, OriGene), HGF (0.1 µg) (pCMV6-XL4-HGF, OriGene), PD-L1 (0.1 µg) (pCMV6-myc-DDK-PD-L1, Origene) were transferred into pIRES (Clontech) or pSF-CMV-CMV-SbfI (Oxford Genetics) by specific restriction enzyme linker (EcoR1 and Nhe1 in TK, BamH1 and Not1 in PD-1) to build as the construct of pSF-PD-L1-Akt, pSF-PD-L1-HGF, pSF-Akt-GFP, pSF-HGF-GFP, pSF-PD-L1-GFP, etc., which was transfected into UMSCs, ADSCs or BMSCs by XtremeGene HP DNA (Roche) as a manufacturer's instruction to engineer as the UMSC-PD-L1-Akt, UMSC-PD-L1-HGF, UMSC-Akt-GFP, UMSC-HGF-GFP, and UMSC-PD-L1-GFP.

Lenti-Viral Plasmids

Lentivector (pLAS3w), and packaging (psPAX2)/envelope plasmids (pMD2.G) were obtained. The cDNA encoding full-length human Akt, PD-L1, Luciferase (Luc) and control GFP was recombinant from the cDNA (pCMV6-myc-DDK-Akt, pCMV6-XL4-HGF, pCMV6-myc-DDK-PD-L1 and pRMT-Luc, OriGene), which were transferred into pUltra (Addgene) or pSF-CMV-CMV-Sbf1 (Oxford Genetics) by specific restriction enzyme linker to build as the construct of pUltra-PD-L1-Akt, pUltra-PD-L1-HGF, pUltra-Akt-GFP, pUltra-HGF-GFP, pUltra-PD-L1-GFP. Subsequently, these templates were amplified by PCR using specific primers, and digested with restriction enzymes sub-cloned to lentiviral vector backbone plasmid pLAS3w. To produce the recombinant lentivirus carrying PD-L1-Akt, Akt, PD-L1, Luc and control GFP, the recombinant plasmid and vector were co-transfected with packaging and enveloping plasmids into 293T cells at a ratio of 3:3:1 by XtremeGene HP DNA (Roche) transfection. The culture supernatant containing the virus particles was collected after 36 hours and again after another 24 hours at half the volume, which was then centrifuged at 15,000 rpm/min for 10 min to remove debris, and then transferred into a 36-mL ultra-centrifuge tube for ultra-centrifugation at 25,000 rpm/min for 3 h. The pellet containing lentivirus was resuspended. Viruses were thawed immediately before titer and cell transduction. UMSCs were infected with the appropriate lentivirus where gene transfer efficiency reached at least 80%.

Lenti-Virus Transduction

Lenti-viral plasmids transductions were done in six-well plates. Unless otherwise specified, UMSCs were seeded at $1 \times 10^5$ cells per well in triplicate at a final volume of 1 ml per well with a multiplicity of infection (MOI) of 5. Protamine sulfate (Sigma-Aldrich) from a 5 mg/ml stock solution (in DMEM-LG, sterile filtered) was added to obtain the desired final concentration. Cells were transduced for 24 hours before being replaced with 1.5 ml per well to build as UMSC-PD-L1-Akt, UMSC-Akt-GFP, UMSC-Luc and UMSC-PD-L1-GFP. Overgrown cells were inoculated onto a six-well plate for drug screening using 1.0 mg/ml G418 or puromycin solutions (Sigma). The medium was replaced every 2 days. The expression of green fluorescent protein (GFP) was observed using inverted fluorescence microscopy based on the color of the medium and the cell state. Following 7 days of screening, the complete medium without puromycin was replaced and cultivation was continued.

Construction of the piggyBac Transposon System for Stable Cell Lines

A piggyBac vector pPB-CMV-MCS-EF1α-RedPuro, which contains the multiple cloning sites (MCS), piggyBac terminal repeats (PB-TRs), core insulators (CIs) and puromycin selection maker (BSD) fused with RFP driven by the human EF1α, was used as the base vector (System Bioscience). DNA fragment containing PD-L1-Akt, PD-L1-HGF, Akt, HGF or PD-L1 (from pUltra-PD-L1-Akt, pUltra-PD-L1-HGF, pUltra-Akt, pUltra-HGF, pUltra-PD-L1) was PCR amplified and subcloned into the pPB-CMV-MCS-EF1α-RedPuro vector, in front of the coding region of EF1α. Detailed information regarding vector constructions (pPB-PD-L1-Akt, pPB-PD-L1-HGF, pPB-Akt, pPB-HGF, pPB-PD-L1) is available upon request. To generate UMSCs stable cells, the above pPB-PD-L1-Akt, pPB-PD-L1-HGF, pPB-Akt, pPB-HGF, pPB-PD-L1 vectors were co-transfected with a piggyBac transposase expression vector (System Biosciences) into UMSCs, ADSCs and BMSCs cells by calcium phosphate (Invitrogen) or by electroporation (Amaxa Nucleofector II, Lonza). Stably cells were selected in the presence of puromycin.

In Vitro Proliferation, Migration and Differentiation Assays

For examining the cellular proliferation and migration, the CFSE staining protocol and transwell migration assays were performed for comparison of UMSC-PD-L1Akt or UMSCs. Proliferation of UMSC-Akt-PD-L1 or UMSCs was tested by applying a CFSE staining protocol to evaluate the effects of on their proliferation. CFSE-stained UMSC-Akt-PD-L1 was seeded at a density of $2 \times 10^4$ cells/mL in 37° C. with 5% CO2 for 5 days. The general gating strategy for proliferating cells was the same as that used for PBMC. The fluorescence measured in this proliferating gate corresponds to the proliferative activity during the 5-day experiment. After the acquisition, all gating and data analyzes were performed using the FlowJo 8.7 software.

Cell migration assay was assessed as described previously with modifications. In brief, UMSC-Akt-PD-L1 or UMSCs were placed in 100 µL in the upper chamber (transwell: 6.5-mm diameter, 5.0-mm pore size) according to the manufacturer's instructions (Costar, #3421). We used SDF-1α (100 ng/mL, R&D System, positive control) in the lower chambers. The assays were conducted over a 4-h incubation period at 37° C. in a 5% $CO_2$ incubator. Because almost all cells stay at the lower side of the membrane after migration, quantification can be performed by simply counting these cells. Adhered cells at the lower side of the membranes were counted under microscope as previously described.

Adipogenic differentiation was induced according to the method described previously. In brief, confluent monolayer cultures of UMSC-Akt-PD-L1 or UMSCs were grown in adipogenic differentiation medium, consisting of DMEM-high glucose (DMEM-HG, Sigma), 100 U/mL penicillin, 100 mg/mL streptomycin, 100 mM insulin (Sigma), 500 mM 3-isobutyl-1-methylxanthine (Sigma), 1 mM dexamethasone (Sigma), 100 mM indomethacin (Sigma) and 10% FCS. Cells maintained in ordinary UMSCs medium served as a negative control. The adipogenic differentiation was changed three times per week. To assess adipogenic differentiation, cells were stained with 0.3% oil red O (Sigma) for 10 min at room temperature, (to label intracellular lipid accumulation), and counterstained with haematoxylin.

To induce osteogenic differentiation, confluent monolayer UMSC-Akt-PD-L1 or UMSCs cultures were grown in DMEM-high glucose (DMEM-HG, Sigma) containing 100 U/mL penicillin (Sigma), 100 mg/mL streptomycin (Sigma), 50 mg/mL L-ascorbic acid 2-phosphate (Sigma), 10 mM b-glycerophosphate (Sigma), 100 nM dexamethasone (Sigma) and 10% FCS. Cells maintained in ordinary UMSCs medium were served as negative controls. The osteogenic differentiation medium was changed three times per week. Levels of osteogenesis were determined using Alizarin red S staining (1%, Sigma) to detect calcium mineralization.

Chondrogenic differentiation of UMSC-Akt-PD-L1 or UMSCs was induced using a high-density pellet cell culture system. Cells were washed in serum-free chondrogenic differentiation medium consisting of DMEM-HG, 100 U/mL penicillin, 100 mg/mL streptomycin, 50 mg/mL L-ascorbic acid 2-phosphate, 40 mg/mL proline (Sigma), 100 mg/mL sodium pyruvate (Sigma), 100 nM dexamethasone, and ITS-plus (10 mg/ml bovine insulin, 5.5 mg/ml transferrin, 5 mg/ml sodium selenite, 4.7 mg/ml linoleic acid, and 0.5 mg/ml bovine serum albumin, Sigma). Aliquots of 250,000 cells were resuspended in chondrogenic differentiation medium and, centrifuged at 250×g and then 10 ng/mL TGF-β1 (R&D Systems) were added. Pellets maintained in chondrogenic differentiation medium without TGF-β1 served as negative controls. Medium was changed twice per week. Chondrogenic differentiation of pellet cultures was confirmed histologically using Alcian blue staining (Sigma) of sulfated proteoglycans. In addition, endothelial cells were induced to differentiate to vascular tubes formation by culturing UMSC-Akt-PD-L1 or UMSCs for 2-3 d in EBM (Cambrex) on 24-well plates precoated with Matrigel (300 μL/well; Becton Dickinson) and vascular endothelial growth factor (VEGF, 10 ng/ml, Sigma) as described previously.

To induce neuronal cell differentiation, UMSC-Akt-PD-L1 or UMSCs was incubated with DMEM using a three-step method with modification. Briefly, in the neuronal induction step, cells were plated at low density on 6-well plates containing fibronectin (Sigma), and then were exposed sequentially to (1) DMEM-HG (Sigma), containing 10% FCS, and 10 ng/mL bFGF (R&D System) for 24 h, (2) in the neuronal commitment step, DMEM-HG containing, 1 mM β-mercaptoethanol (βME, Sigma), and 10 ng/mL NT-3 (R&D Systems) for 2 days, and (3) in the neuronal differentiation step, DMEM-HG that containing NT-3 (10 ng/mL, R&D Systems), NGF (10 ng/mL, R&D Systems) and BDNF (50 ng/mL, R&D Systems) for 3 to 7 days. Following cell differentiation, the cells were left for immunohistochemical analysis.

Flow-Cytometry

For the analysis of the cell surface-marker expression, cells were detached with 2 mM EDTA in PBS, washed with PBS containing BSA (2%) and sodium azide (0.1%), and then incubated with the respective antibody conjugated with fluorescein isothiocyanate (FITC) or phycoerythrin (PE) until analysis. As a control, cells were stained with mouse IgG1 isotype-control antibodies. The antibodies to PD-1, PD-L1, CD3, CD8, CD4, CD25, Foxp3, CD44, CD45, CD11b, F4/80, IFN-γ, CD206 and GFP for flow cytometry were purchased from BD Biosciences. Cells were analyzed using a FACScan (BD) with the CellQuest Analysis (BD Biosciences) and FlowJo software v.8.8 (TreeStar Inc.). Results are expressed by the percentage of positively stained cells relative to the total cell number. For quantitative comparison of surface protein expression, the fluorescence intensity of each sample was presented as median fluorescence intensity (MFI). For intracellular staining of Ki-67 and granzyme B, TILs were cultured in the presence of 1 μg/ml of anti-CD3 for 48 h. Cells were then incubated with anti-CD8 before permeabilization with Triton ×100 and then stained with antibody against Ki-67 (Millipore) and Granzyme B. Data were analyzed using a FACScan (BD) with the CellQuest Analysis (BD Biosciences) and FlowJo v.8.8 (TreeStar).

Hypoxia Procedure

UMSC-Akt-PD-L1 or UMSCs ($1×\square10^5$/mL) cultured at 37° C. in 5% $CO_2$-humidified incubators were treated in normoxic (21% $O_2$) or hypoxic conditions (1% $O_2$) for different time points. Hypoxic cultures were cultivated in a two-gas incubator (Jouan, Winchester, Virginia) equipped with an $O_2$ probe to regulate $N_2$ levels. Cell number and viability were evaluated using a trypan blue exclusion assay and TUNEL assay.

Measurement of Cell Death Induced by $H_2O_2$

The viability of UMSCs was determined by MTT (C,Ndipheyl-N-4,5-dimethyl thiazol-2-yl tetrazolium bromide, Sigma) assay. UMSCs were cultured in a 96-well microplate. After incubation with $H_2O_2$ for 1 h, the media were replaced with MTT solution (5 mg/mL in PBS). Incubation was further continued for 4 h, and then the supernatant was removed by aspiration. Dimethyl sulfoxide (DMSO, Sigma) was added and absorbance was read at 570 nm on microplate reader (Molecular Devices), and the percentage of cell viability was obtained. Moreover, DCFH-DA (Sigma), a non-polar compound, enters the cell and is cleaved to form DCFH which is trapped to be oxidized by oxygen free radicals to produce fluorescent DCF. UMSCs were preincubated in serum free DMEM for 24 h, treated with $H_2O_2$ for 30 min, and preloaded with 10 μM DCFH-DA for 30 min at 37° C. Fluorescence intensity was analyzed by fluorescence reader (Finland) using 485 nm excitation and 538 nm emission filter.

In Vitro Analysis of Antigen-Specific T-Cell Responses

Splenocytes ($2×10^6$) from BALB/c mice were cultured on 24-well plates in RPMI-1640 media (Gibco) supplemented with 10% FBS (Sigma), 1% penicillin/streptomycin (Gibco). Then, splenocytes cocultured with different ratio (10:1 or 1:1) of cells ($2×10^5$ or $2×10^6$) were either left unstimulated or incubated with CD3-CD28 beads (Dyna-beads, Thermo). For proliferation assays, splenocytes were stained with Carboxyfluorescein succinimidyl ester (CFSE) (Invitrogen). We estimated the proliferation/division of cells using the Proliferation Index (PI), which can be calculated by a formula: PI=The total numbers posterior to proliferation/The total numbers prior to proliferation. After 6-day-culture cells were harvested and stained to analyse proliferation of Treg, CD4− and CD8− T cell subsets. Alternatively, to analyse proliferation after a 6-day culture in longitudinal samples for which cell numbers were limited, non-CFSE stained splenocytes were cultured, and stained with Ki67 or isotype control antibodies. Fold change in proliferation (FC proliferation) was calculated as a ratio of proliferation under UMSC-TRAIL-TK-PD-1 conditions divided by proliferation under control conditions.

TUNEL Assay

Cellular apoptosis was assayed by immuno-histochemistry using a commercial TUNEL staining kit (DeadEnd Fluorimetric TUNEL system; Promega). The percentage of TUNEL labeling was expressed as the number of TUNEL-positive nuclei divided by the total number of nuclei stained with DAPI.

Animal Brain Ischemia/Reperfusion Model

Adult male Sprague-Dawley rats (weight 250-300 g) were used in this study. Animals were subjected to three-vessel ligation. All surgical procedures, animals' experimental protocols and methods were carried out in accordance with the Institutional guidelines and were approved by the Institutional Committee of Animal and Clinical Research of China Medical University, Taichung, Taiwan. The rats were anesthetized with chloral hydrate (0.4 g/kg, ip). Ligation of the right middle cerebral artery (MCA) and bilateral common carotids (CCAs) was performed. The bilateral CCAs were clamped with non-traumatic arterial clips. Using a surgical microscope, a 2×2 mm craniotomy was drilled where the zygoma fuses to the squamosal bone. The right MCA was ligated with 10-0 nylon suture. Cortical blood flow was measured continuously with a laser Doppler flowmeter (PF-5010, Periflux system, Sweden) in anesthetized animals. A burr hole (1-mm diameter) was made in the right fronto-parietal region to allow placement of photodetectors. A probe (0.45 mm in diameter) was stereotaxically placed in the cortex (1.3 mm posterior, 2.8 mm lateral to the bregma, and 1.0 mm below the dura). After 90 minutes of ischemia, the suture on the MCA and arterial clips on CCAs were removed to allow reperfusion. Core body temperature was monitored with a thermistor probe and maintained at 37° C. with a heating pad during anesthesia. After recovery from anesthesia, body temperature was maintained at 37° C. with a heat lamp.

Intracarotid and/or Intravenous Transplantation of UMSC-PD-L1-Akt, or UMSC-PD-L1-HGF, ADSC-PD-L1-Akt or BMSC-PD-L1-Akt At two hours after brain ischemia, adult male Sprague-Dawley rats (200-250 g) were anesthetized with chloral hydrate (0.4 g/kg, ip) and treated with approximately $1 \times 10^6$ cells (UMSC-PD-L1-Akt, UMSC-PD-L1-HGF, UMSC-Akt, UMSC-HGF, or UMSC-PD-L1) through intravenous route. The control animals were administered PBS only. For intracarotid injections, the ipsilateral common carotid artery was again exposed, the external carotid artery was ligated with 6-0 silk, the superior thyroid and pterygopalatine arteries were coagulated, and $1 \times 10^5$ UMSC-PD-L1-Akt, UMSC-PD-L1-HGF, UMSC-Akt, UMSC-HGF, UMSC-PD-L1, ADSC-PD-L1-Akt or BMSC-PD-L1-Akt in 500 μL, saline were injected into the internal carotid artery using a 24-G angio-catheter at 24 hours after stroke. Because of the immunosuppressive characteristics of mesenchymal stem cells, rat hosts did not receive any immunosuppressive medication.

Neurological Behavioral Assessment

Behavioral assessments were performed 5 days before cerebral ischemia, and 1, 7, 14 and 28 days after cell transplantation. The tests measured body asymmetry, locomotor activity and grip strength. The baseline-test scores were recorded in order to normalize those taken after cerebral ischemia. The elevated body swing test was used to assess body asymmetry after MCA ligation and evaluated quantitatively. Initially, animals were examined for lateral movement, on their bodies being suspended by their tails 10 cm above the cage floor. The frequency of initial head swing contra-lateral to the ischemic side was counted in twenty continuous tests and was normalized to the baseline score. Locomotor activity measurement was subjected to Versa-Max Animal activity monitoring (Accuscan Instruments, Inc., Columbus, OH) for about 2 hours for behavioral recording. This instrument contained 16 horizontal and 8 vertical infrared sensors. The vertical sensors were situated 10 cm from the floor of the chamber. Motor activity was counted as the number of beams broken by a rat's movement in the chamber. Three parameters of vertical items over 2 hours were calculated: (i) vertical activity (ii) vertical time (iii) number of vertical movements.

Measurement of Infarct Size Using Magnetic Resonance Image (MRI)

MRI was performed on anesthetized rats in the R4 imaging system (GE) at 3.0 T. Brains were scanned in 6-8 coronal image slices, 2 mm thick without gaps. T2-weighted imaging (T2WI) pulse sequences were obtained with the use of a spin-echo technique (repetition time, 4000 ms; echo time, 105 ms). Images were captured sequentially for each animal at 1, 7, and 28 days after cerebral ischemia. To measure the infarction area in the right cortex, we subtracted the noninfarcted area in the right cortex from the total cortical area of the left hemisphere. The area of infarct was drawn manually from slice to slice, and the volume was then calculated by internal volume analysis software (Voxtool, General Electric).

Bioluminescent Imaging (BLI)

Animals were imaged with the IVIS Imaging System 200 Series (Xenogen) to record bioluminescent signal. Animals were anesthetized with isoflurane and received intra-peritoneal injection of D-luciferin (Caliper) at a dose of 270 mg/g body weight. Imaging acquisition was performed at 15 min after intraperitoneal injection of luciferin. For BLI analysis, regions of interest encompassing the intracranial area of signal were defined using an IVIS System (Xenogen), and the total photon flux was recorded. To facilitate comparison of cellular engrafted rates, each animal's luminescence scores were normalized against its own luminescence reading at Day 14, thereby allowing each mouse to serve as its own control.

Isolation of Leukocytes from Spleen and Brain

Spleens from individual control and treated rats were removed and a single-cell suspension was prepared by passing the tissue through a 100-μm nylon mesh (Fisher Scientific). The cells were washed using RPMI 1640 (Invitrogen). RBC (Red cells) were lysed using 1× red cell lysis buffer (eBioscience) and incubated for 3 minutes. Cells were then washed twice with RPMI 1640, counted and resuspended in stimulation medium RPMI containing 2% fetal bovine serum (Gibco) and 0.4% β-ME (Sigma-Aldrich).

Brain was separated into the ischemic (right) and non-ischemic (left) hemispheres, dissociated enzymatically in 3 U/mL recombinant DNase I (Roche) and 1 mg/mL collagenase from *Clostridium histolyticum* (Sigma-Aldrich), resuspended in 80% Percoll (GE Healthcare) and subjected to density gradient centrifugation for 30 minutes at 1600 rpm (400 g) according to a previously described method. 18 Leukocytes were extracted from the interphase and were then washed twice with RPMI 1640, counted and resuspended in stimulation medium. Inflammatory cells from individual brain hemispheres were evaluated by flow cytometry.

Flow Cytometry for T Cell Population

To analyze the cell populations, multicolor flow cytometry was applied for the studies. First, the cells were washed with PBS containing BSA (2%) and sodium azide (0.1%). Subsequently, the cells were incubated with the respective antibody (PD-L1, CD3, CD8, CD4, CD25, Foxp3, CD44, CD45, CD11b, F4/80, IFN-γ, 7AAD and CD206) from BD conjugated with appropriate fluorescent dyes before analysis.

As a control, cells were stained with mouse IgG1 isotype-control antibodies. The gating strategy was performed based on the right justification of first gate, exclusion of doublets by SSC-A and SSC-H, exclusion of dead cells and further selected as being 7-AAD$^+$/FSC-A using a FACScan (BD) with the CellQuest Analysis (BD Biosciences) and FlowJo software v.8.8 (TreeStar Inc.). Results were expressed by the percentage of positively stained cells relative to total cell number. Differences between groups were evaluated by two-way ANOVA with the Newman-Keuls post hoc test. A P value <0.05 was considered significant.

Intracellular Staining

Intracellular staining was performed. In brief, isolated leukocytes were resuspended (2×106 cells/mL) and cultured with LPS (10 μg/mL, Sigma), phorbol 12-myristate 13-acetate (50 ng/mL, Sigma), ionomycin (500 ng/mL and GolgiPlug protein transport inhibitor (BD Biosciences) for 4 hours. Cells were fixed and permeabilized with fixation/ permeabilization buffer (BD Biosciences) according to the manufacturer's instructions. Permeabilized cells were stained with antibodies specific for the following intracellular targets: tumor necrosis factor-α (clone MP6-XT22), interleukin (IL)-10 (clone JESS-16E3), PD-1 (clone J43), and FoxP3 (clone FJK-16s), then resuspended in staining buffer for acquisition. Isotype-matched mAb served as negative controls.

Cytokine Measurement

To measure the level of TNF-α, VEGF, and TGF-β, TILs were isolated from the mice treated with different IO@FuDex formulations at 4 weeks after tumor inoculation. The TILs were further cultured in 6-well plate (2×10$^5$ cells ml$^{-1}$) using PRMI-1640 medium with L-glutamine (2 mM) for 48 h. TNF-α, VEGF, and TGF-β in the culture suspensions were semi-quantified with Quantikine ELISA kit (R&D Systems) under a spectrophotometer (Molecular Devices) and standard curves were generated with the program SOFTmax (Molecular Devices).

Immunohistochemical Assessment

Animals were anesthetized with chloral hydrate (0.4 g/kg, ip) and their brains fixed by transcardial perfusion with saline, followed by perfusion and immersion with 4% PFA. Tissue samples were then harvested, fixed further by immersion in 4% PFA, dehydrated in 30% sucrose, and frozen on dry ice. Coronal sections (6 μm thick) were cut by a cryostat, stained with H&E and observed by light microscopy (E600, Nikon). To identify the expression of cell type-specific markers in Luciferase$^+$ cells, double immunofluorescence was performed. Each coronal section stained first with primary luciferase antibody (1:1000, Novus), MAP-2 (1:200, Millipore), GFAP (1:500, Millipore) and GFP antibody (1:200, Millipore), followed by treatment with specific antibodies reacted to secondary antibody conjugated with Cy3 (1:500; goat anti-rabbit IgG, Jackson Immunoresearch) or FITC (1:500; goat anti-mouse IgG, Jackson Immunoresearch) were double immunostained in order to demonstrate their co-localization in one cell under CLSM.

Assessment of Immune-Related Adverse Events (irAEs)

We evaluated irAEs including: (1) weight monitoring, (2) histology, (3) immune cells infiltration, and (4) liver and kidney function after the treatment of IO@FuDex$^3$ and M-IO@FuDex$^3$. The body weight of the mice were monitored during the treatment. In addition, H&E staining of livers, lungs, spleens, kidneys, and colons sections of the mice treated with the IO@FuDex formulations were evaluated at 4 weeks after tumor inoculation (n=6) for histology analysis. The CD8$^+$ and CD4$^+$ T cells infiltration to liver, colon, kidney, and lung were examined by IHC and scored by counting the numbers of positive cells in ten high power field per mm$^2$. Furthermore, biochemical profiles of the ALT, AST, creatinine and glucose were measured using mouse serum from sequential time points (0, 5 10, 15, 20, 25 and 30 d) of each group (n=6) by a Beckman Unicell DxC800 analyzer.

Rat Model of Acute Myocardial Infarction (AMI) and Treatment Protocol

Adult male Sprague-Dawley rats (SD, 200-250 g) were subjected to AMI by ligation of left anterior descending (LAD) coronary artery. In brief, after induction of anaesthesia with 2% isoflurane in 100% oxygen, rats received artificial ventilation using a respirator (SN-480-7, Japan) with a tidal volume of 1 mL/100 g and respiratory rate of 80/min. A left thoracotomy was performed in the 4-5$^{th}$ intercostal space using a rib retractor (MY-94545, Japan); the left lung was deflated using a small piece of gauze soaked in saline. The pericardium was then removed and an intra-myocardial ligature placed 1-2 mm below the atrio-ventricular groove using a 6-O polyethylene suture needle with thread (Ethicon, UK). Lungs were then re-inflated before the thorax was closed. Sham rats underwent the same protocol with the exception of the ligation of the coronary artery.

Intravenous and/or Intracarotid Transplantation of UMSC-PD-L1-Akt, UMSC-PD-L1-HGF, ADSC-PD-L1-Akt or BMSC-PD-L1-Akt At two hours after AMI, rats were anesthetized with chloral hydrate (0.4 g/kg, ip) and treated with approximately 1×10$^6$ cells (UMSC-PD-L1-Akt, UMSC-PD-L1-HGF) through intravenous route. The control animals were administered PBS only. For intracarotid injections, the left common carotid artery was exposed, the external carotid artery was ligated with 6-0 silk, the superior thyroid and pterygopalatine arteries were coagulated, and 0.5×10$^6$ UMSC-Akt-PD-L1, UMSC-PD-L1-HGF, ADSC-PD-L1-Akt or BMSC-PD-L1-Akt in 500 μL saline were injected into the internal carotid artery using a 30-G angio-catheter at 24 hours after AMI.

Myocardial Histology and Immunohistochemical Analysis

Experimental rats were re-anesthetized with chloral hydrate (0.4 g/kg IP), and were sacrificed at 3 days and 28 days after AMI. Three rats without LAD ligation were used as normal controls. Rat hearts were fixed in 4% paraformaldehyde with immersion in 30% sucrose for 3 days. A series of adjacent 6-μm-thick sections were cut by cryostat from each tissue block in the coronal plane, stained with H&E, and analyzed by light microscopy (Nikon, E600). Masson trichrome (Sigma)-stained sections at various levels (apex, mid-LV and base) along the long axis were analyzed for calculating infarct size, wall thickness and percentage of fibrosis using ImageJ software (NIH). Infarct size was measured as percentage of the LV circumference from Masson trichrome stained sections at 28 days post-MI. Grading of inflammation and fibrosis were examined in a blind manner using light microscopy by a scoring system: grade 0, no inflammation or fibrosis; grade 1, cardiac infiltration or fibrosis in up to 5% of cardiac sections; grade 2, 6% to 10%; grade 3, 11% to 30%; grade 4, 31% to 50%; and grade 5, >50%.

Each coronal section was stained with primary CD68 (1:200, Millipore) for inflammatory cell infiltration (CD68-positive) assessed at 10 randomly selected high visual fields in the border zone of infarcted myocardium and expressed as number per high-power visual field. The tissue sections were analyzed with a Carl Zeiss LSM510 laser-scanning confocal microscope. FITC (green, 1:500; Jackson Immunoresearch), Cy3 (red, 1:500; Jackson Immunoresearch) and Alexa Fluor 680 (blue, 1:1000; Invitrogen) fluorochromes on the immunofluorescence-labeled slides were excited by laser beam at 488 nm, 543 nm and 680 nm.

Statistical Analysis

All measurements in this study were performed in a blinded design. Results were expressed as mean±SEM. Two-tailed Student's t tests were used to evaluate the significance of mean differences between the control and the treated group. Differences between groups were evaluated by two-way ANOVA with the Newman-Keuls post hoc test. A P value <0.05 was considered significant.

Example 1 In Vitro Characterization of UMSCs and UMSC-Akt-PD-L1

Figure 1B:
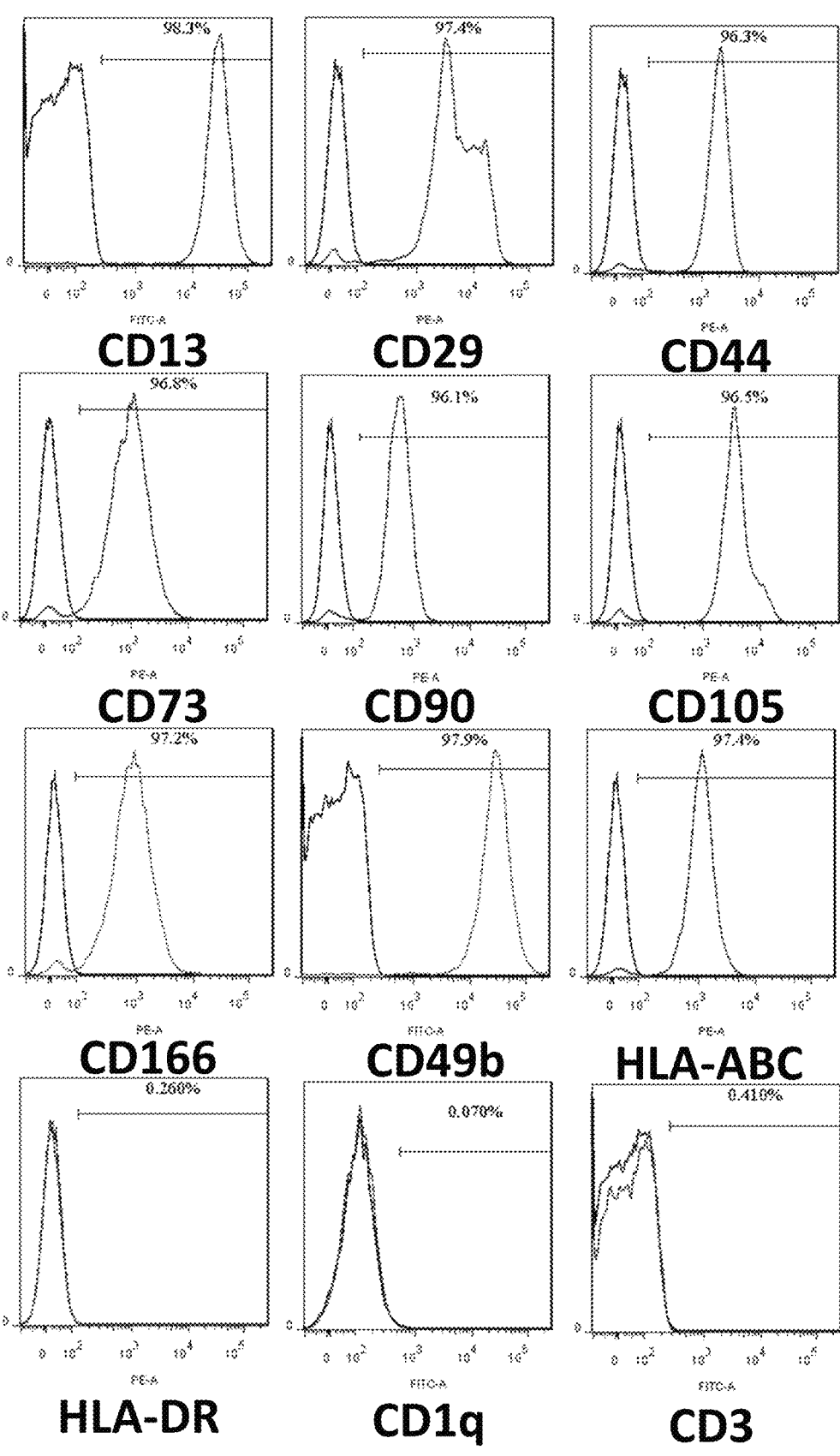
FIG. 1B shows the biological characteristics of a primary culture of umbilical cord mesenchymal stem cells revealed by flow cytometry.
Figure 1B:
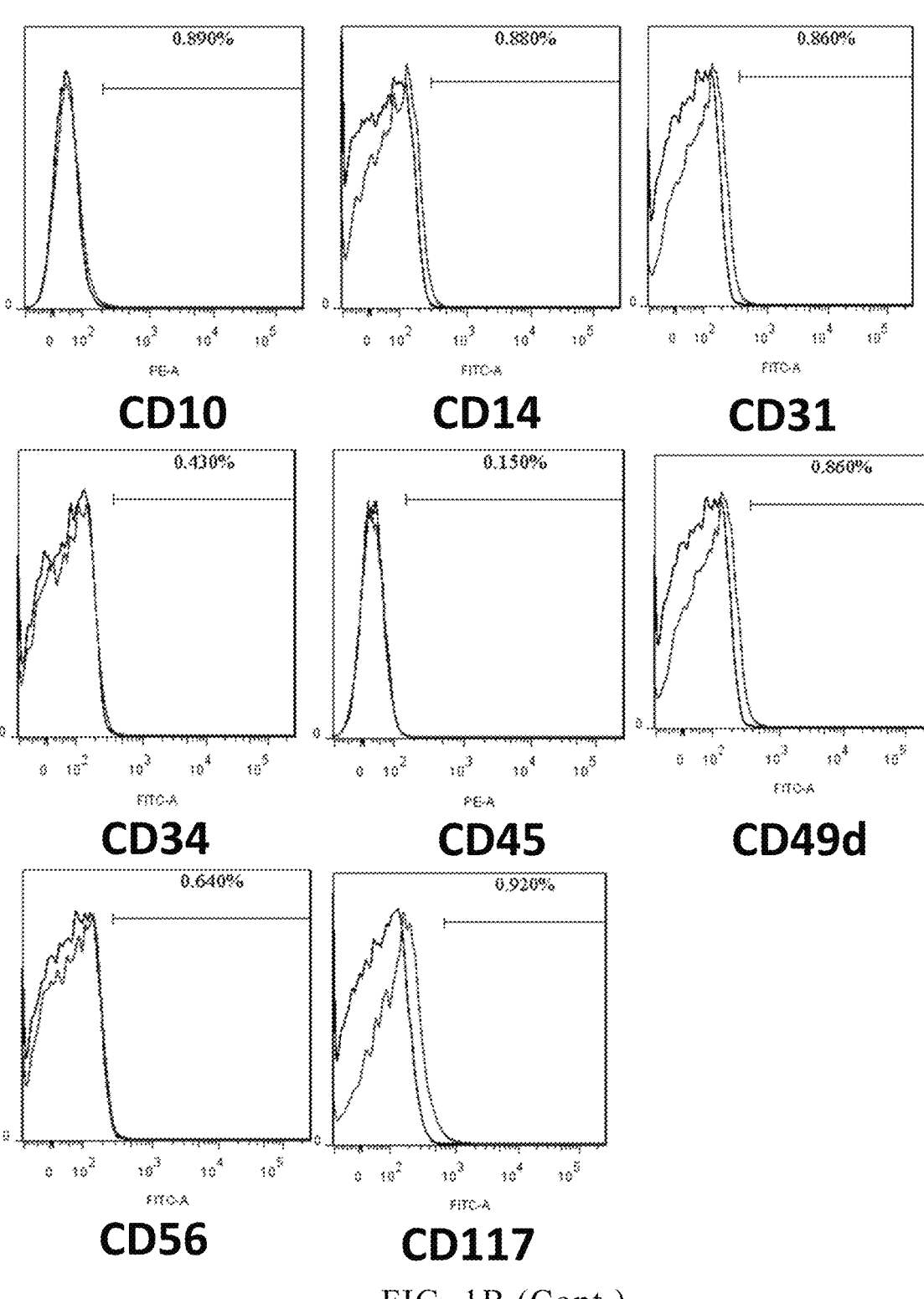

We prepared the primary cultures of umbilical cord mesenchymal stem cells (UMSCs) from Wharton's jelly (WJ) and analyzed the cell morphology and biological properties (FIG. 1A). The flow cytometry revealed that the cells were negative for CD1q, CD3, CD10, CD14, CD31, CD34, CD45, CD49d, CD56, CD117 and HLA-DR, but positive for CD13, CD29, CD44, CD73, CD90, CD105, CD166, CD49b and HLA-ABC (FIG. 1B). These observations indicate that UMSCs have the same surface markers as those of mesenchymal stem cells (MSCs), consistent with observations of bone marrow MSCs.

Figure 1C:
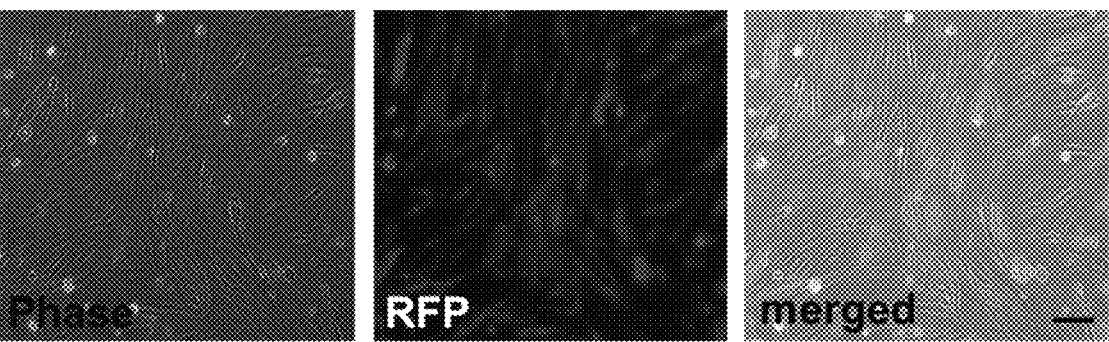
FIG. 1C shows the RFP fluorescence and PD-L1 expression levels of UMSC-PD-L1-Akt detected by flow cytometry.
Figure 1C:
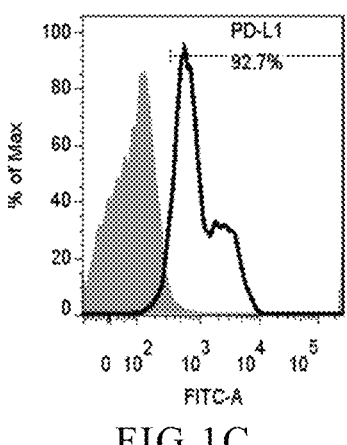
Figure 1D:
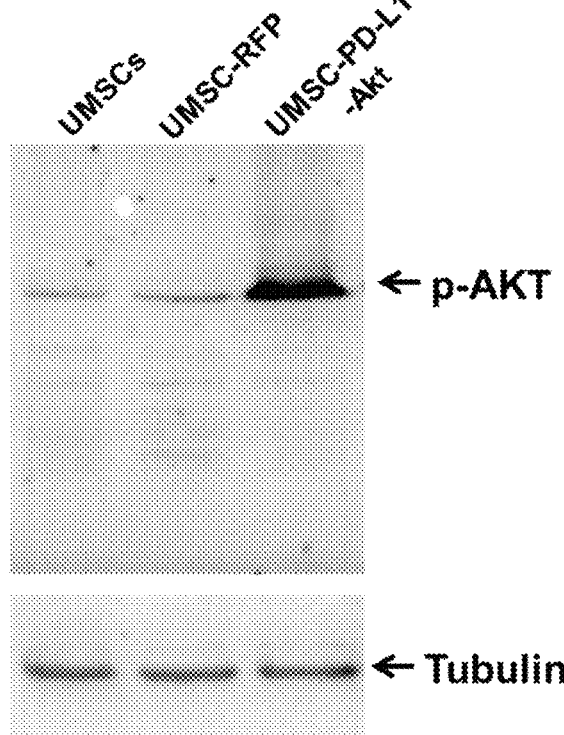
FIG. 1D shows the Akt expression level of UMSC-PD-L1-Akt detected by Western blot method.
Figure 1E:
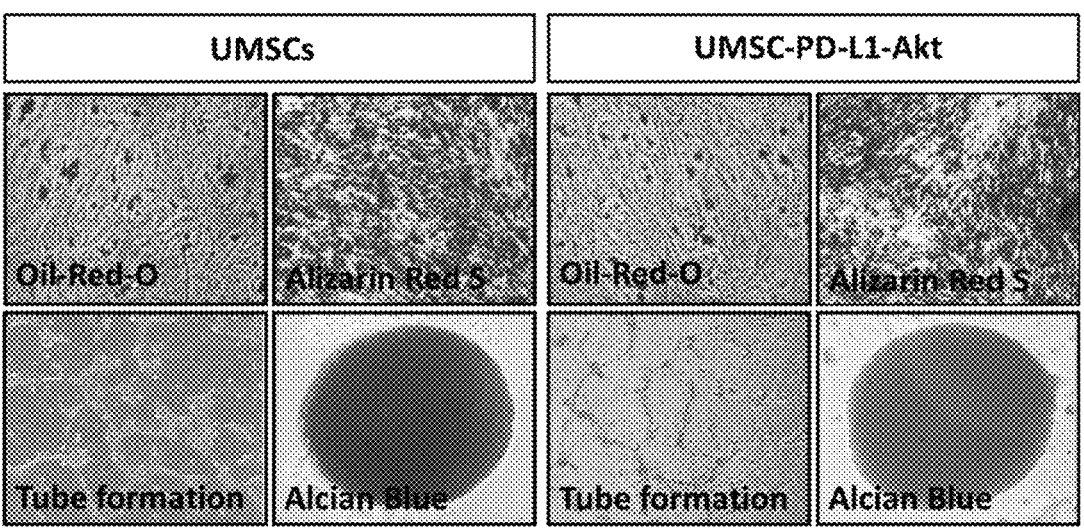
FIG. 1E shows the microscopic observation results of adipogenesis, chondrogenesis, osteogenesis and vascular tube formation of UMSC-Akt-PD-L1 and common UMSCs.

To evaluate the UMSCs transfection efficacy, the RFP fluorescence and PD-L1 expression level of UMSC-PD-L1-Akt were analyzed by flow cytometry study. At 36 h to 48 h after transfection, it demonstrated that the uptake efficacy was average 55-65% via the results of RFP and PD-L1 flow cytometry (FIG. 1C). Subsequently, after 3-5 days puromycin screening, over 90% cells were fully transduced with the transgenes (FIG. 1C). In western blot, significant increase of Akt-transgene expression was also observed on the UMSC-PD-L1-Akt (FIG. 1D).

To determine UMSC-PD-L1-Akt-Luc survival in vivo, a direct correlation between cell number of the Luc-expressing UMSCs signal intensity in vitro and in vivo within the ranges tested was observed. UMSC-PD-L1-Akt-Luc retained luciferase expression through over 100-150 days (FIG. 1D). These experiments demonstrate that MSCs can be efficiently and stably transduced with piggyBac transposone, and that genetic modification by transposon does not result in altering DNA copy number and arrangement of UMSCs.

To demonstrate whether UMSC-PD-L1-Akt still possess multipotent differentiation potential, we analyzed the adipogenic, chondrogenic, osteogenic and vascular tube formation, which demonstrated that the UMSC-Akt-PD-L1 displayed similar behavior to the plain UMSCs without PD-L1-Akt-transgene transduction (FIG. 1G).

Example 2 Enhanced Proliferation of UMSC-PD-L1-Akt

Figure 2A:
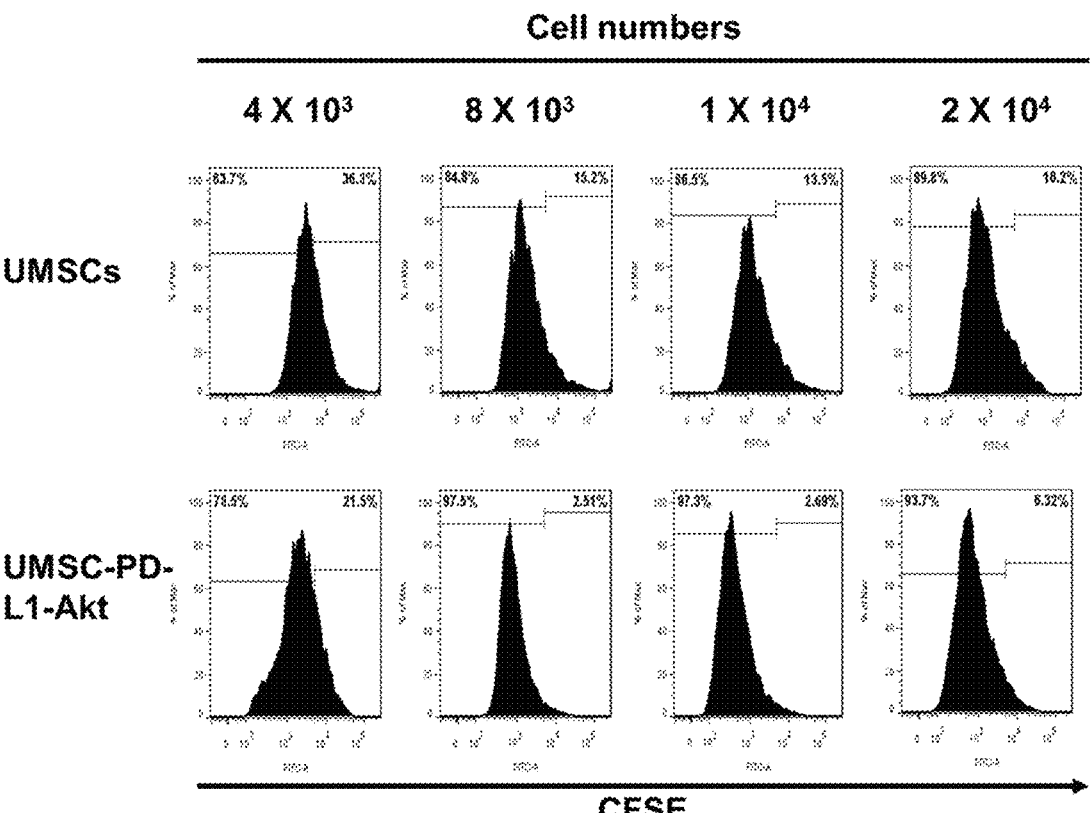
FIG. 2A shows the proliferation results of UMSC-Akt-PD-L1 and common UMSCs by CFSE staining.

To demonstrate the proliferation effect, CFSE assays were examined for biological characteristics of UMSC-PD-L1-Akt. Significant increased proliferation, as observed by the percentage of proliferating cells in the CFSE assays, did not affect cell viability, and was observed in the UMSC-PD-L1-Akt compared to UMSCS (FIG. 2A).

Example 3 Enhancement of UMSC-PD-L1-Akt Survival in $H_2O_2$-Induced Apoptosis

Figure 2B:
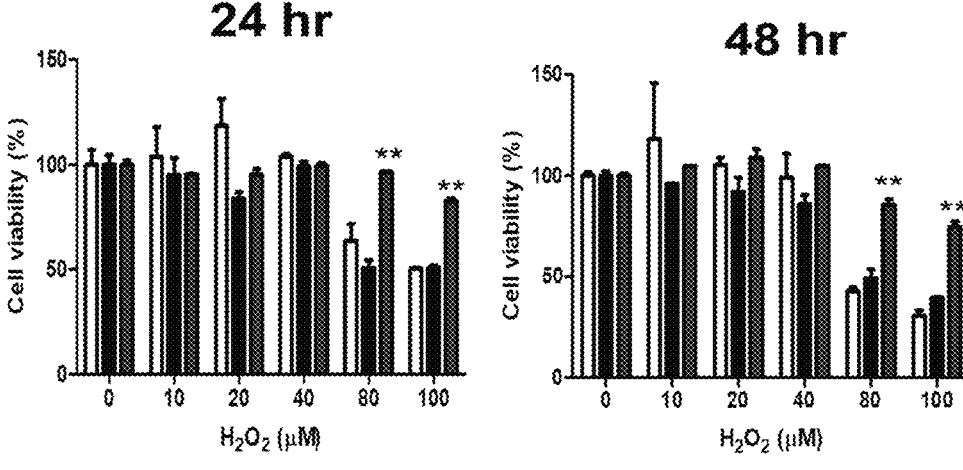
FIG. 2B shows the cell viability results of UMSC-Akt-PD-L1, UMSC-Luc and UMSCs treated with $H_2O_2$.
Figure 2B:
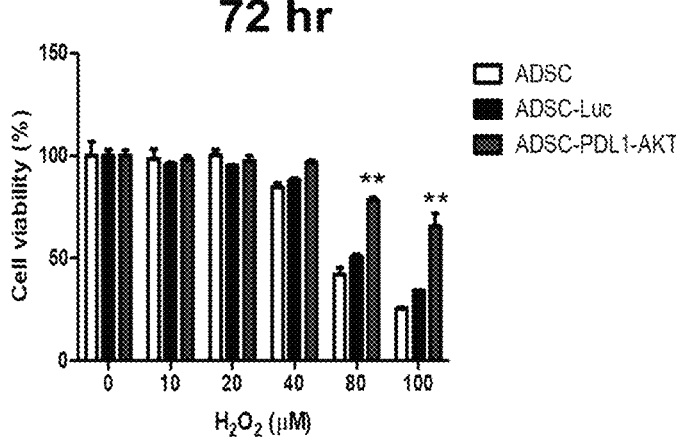
Figure 2C:
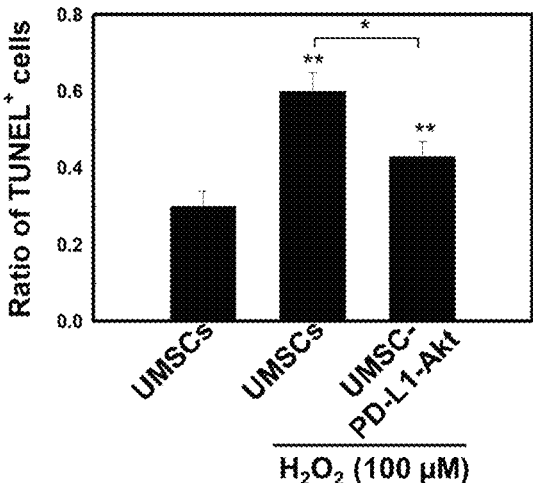
FIG. 2C shows the cell ratio of TUNEL+ of UMSC-Akt-PD-L1, UMSC-Luc and UMSCs treated with $H_2O_2$.
Figures 2D, 2E:
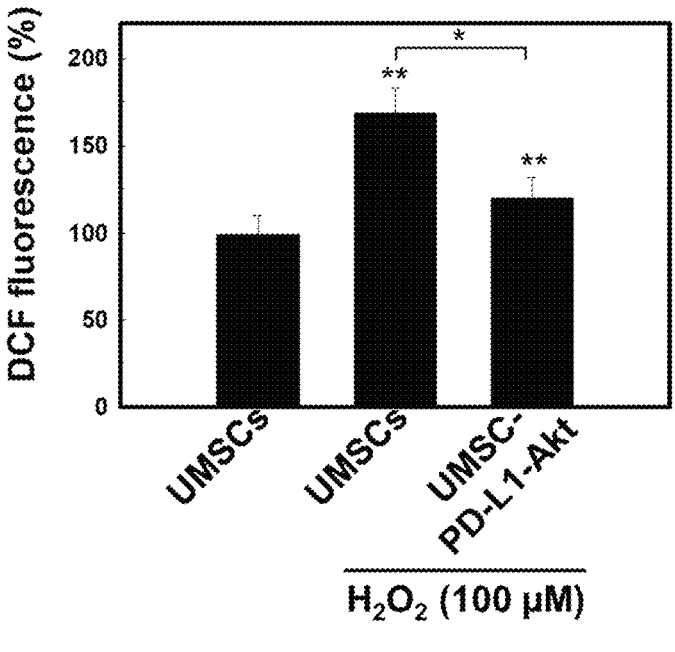
FIG. 2D shows the results of intracellular reactive oxygen species (ROS) levels of UMSC-Akt-PD-L1, UMSC-Luc and UMSCs treated with $H_2O_2$ in DCF fluorescence analysis.
FIG. 2E shows the results of Akt phosphorylation of UMSC-Akt-PD-L1, UMSC-Luc and UMSCs treated with $H_2O_2$ by Western blot method.

To determine the mechanism of enhanced cell survival, the effects of the apoptotic stimulus of $H_2O_2$ was evaluated on UMSC-PD-L1-Akt in vitro. UMSC-PD-L1-Akt was more resistant to $H_2O_2$-induced cell death in a dose-dependent manner (0, 1, 10, 100 μM) than UMSC-Luc and control UMSCs (FIG. 2B). Significant reduction of TUNEL$^+$ cell was observed in the UMSC-PD-L1-Akt after $H_2O_2$ administration compared to the UMSCs (FIG. 2C). The intracellular level of reactive oxygen species (ROS) analyzed by fluorescent DCF after $H_2O_2$ revealed significantly reduced UMSC-PD-L1-Akt compared to UMSCs (FIG. 2D). In western blot analysis, Akt level was induced to be phosphorylated 30 min after $H_2O_2$ in both UMSCs and UMSC-PD-L1-Akt (FIG. 2E). Importantly, phosphorylated Akt level returned to near basal level in UMSCs, but remained significantly elevated after 3 h in UMSC-PD-L1-Akt (FIG. 2E).

Figure 3A:
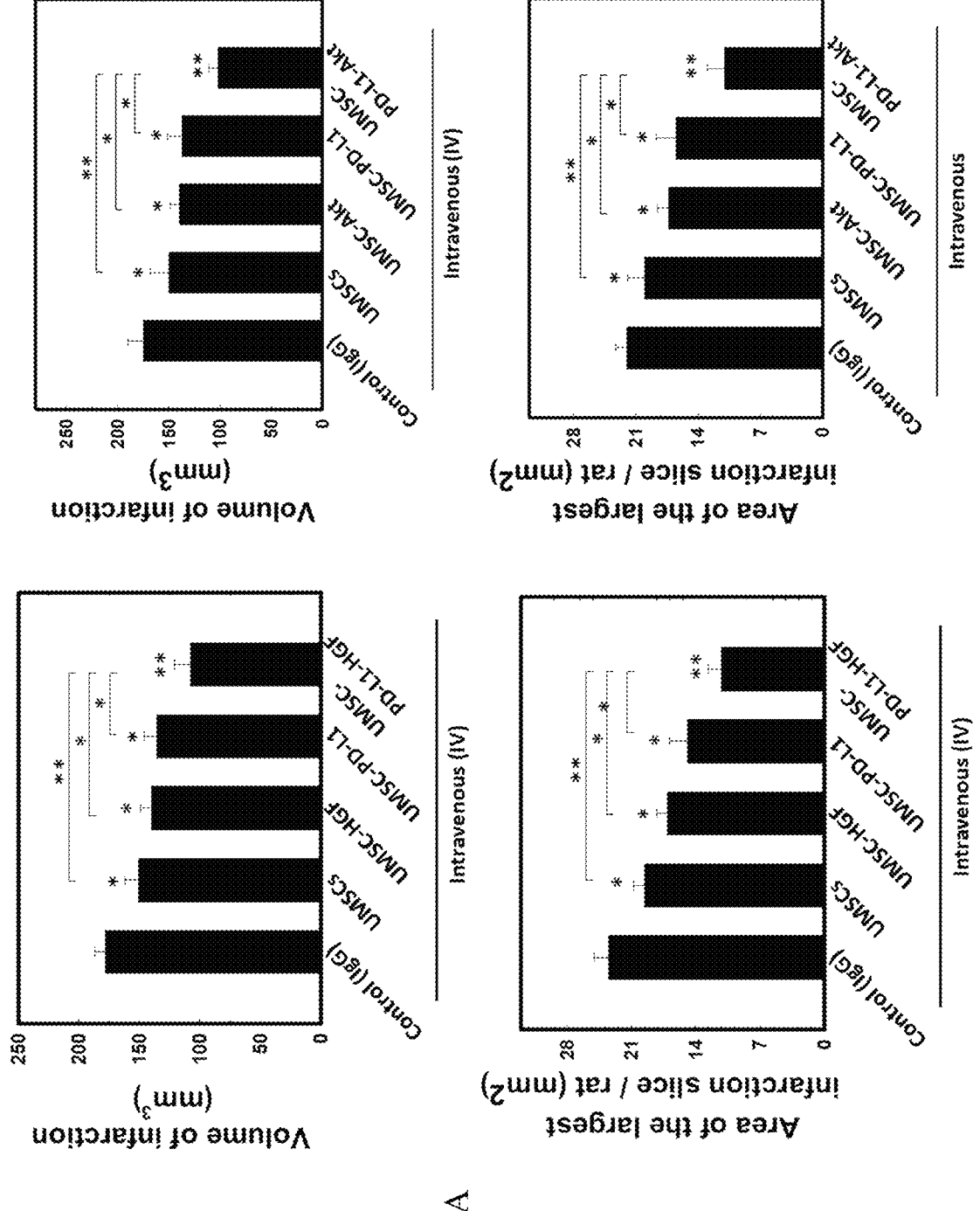
FIG. 3A shows the results of intravenous injection of IgG, UMSCs, UMSC-Akt, UMSC-HGF, UMSC-PD-L1, UMSC-PD-L1-Akt or UMSC-PD-L1-HSF in the infarct area after a stroke.
Figure 3B:
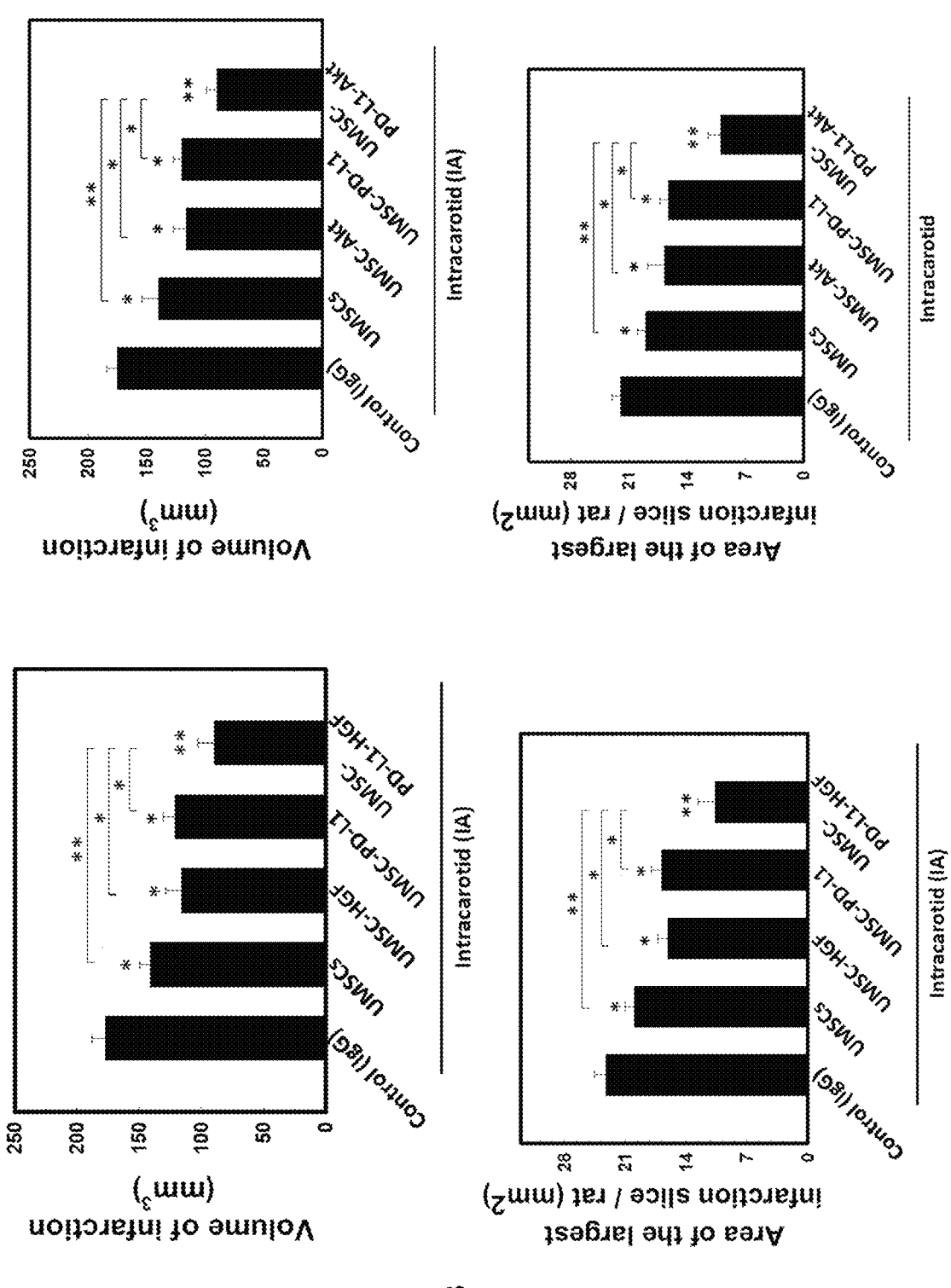
FIG. 3B shows the results of intracarotid injection of IgG, UMSCs, UMSC-Akt, UMSC-HGF, UMSC-PD-L1, UMSC-PD-L1-Akt or UMSC-PD-L1-HSF in the infarct area after a stroke.
Figure 3C:
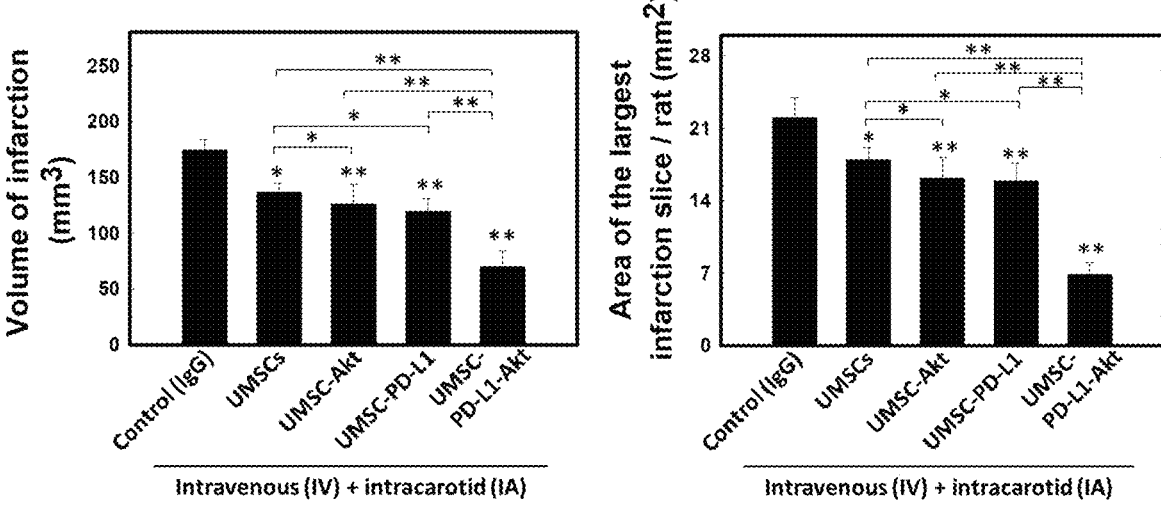
FIG. 3C shows the results of combined intravenous and intracarotid injection of IgG, UMSCs, UMSC-Akt, UMSC-PD-L1 or UMSC-PD-L1-Akt in the infarct area after a stroke.
Figure 3D:
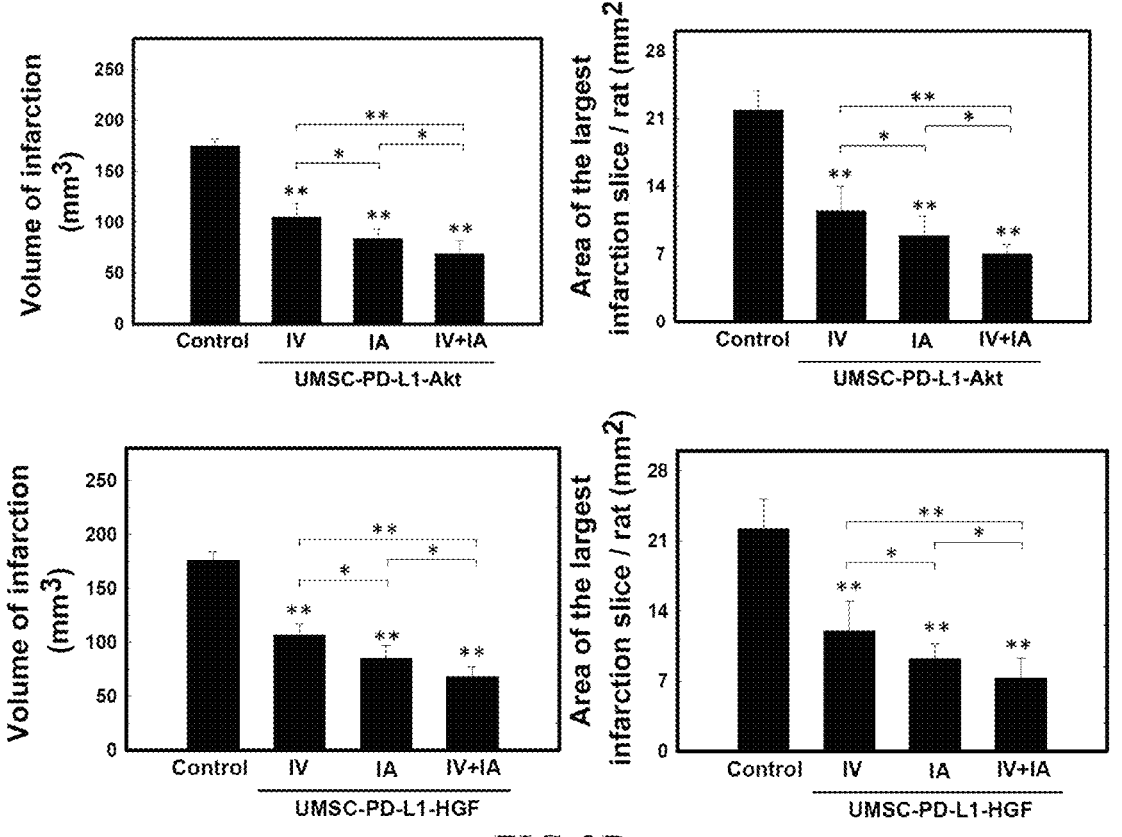
FIG. 3D shows the results of infarct area after a stroke in intravenous (IV), intracarotid (IA) and combined intravenous and intracarotid (IV+IA) injections of UMSC-PD-L1-Akt or UMSC-PD-L1-Akt and in a control group.
Figure 3E:
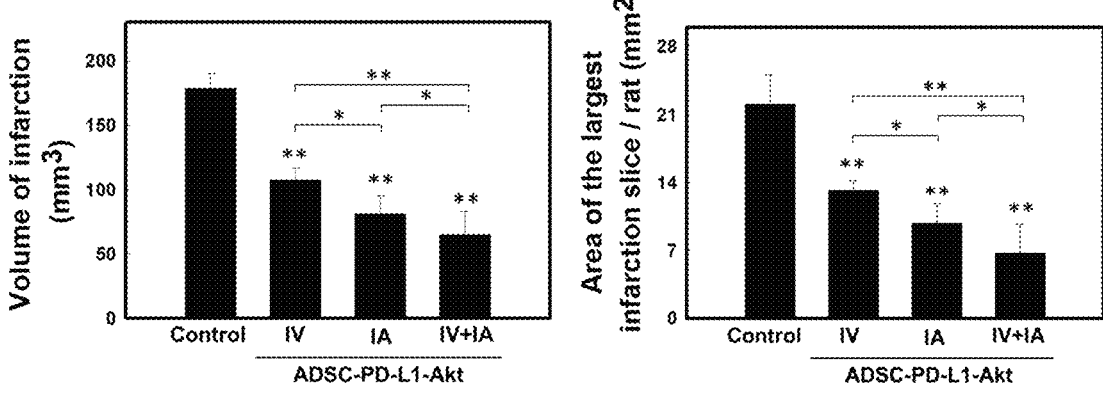
FIG. 3E shows the results of infarct area after a stroke in intravenous (IV), intracarotid (IA) and combined intravenous and intracarotid (IV+IA) injections of ADSC-PD-L1-Akt and in a control group.
Figure 3F:
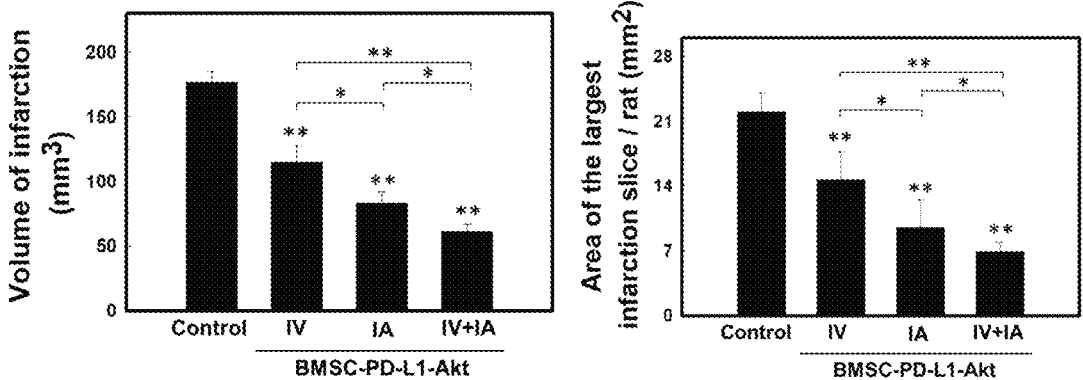
FIG. 3F shows the results of infarct area after a stroke in intravenous (IV), intracarotid (IA) and combined intravenous and intracarotid (IV+IA) injections of BMSC-PD-L1-Akt and in a control group.

Example 4 Reduction of Infarct Volume after Intra-Carotid Combined with Intravenous UMSC-PD-L1-Akt, UMSC-PD-L1-HGF, ADSC-PD-L1-Akt or BMSC-PD-L1-Akt Transplantation We first demonstrated that either intravenous or intracarotid UMSC-PD-L1-Akt or UMSC-PD-L1-HGF (IV-UMSC-PD-L1-Akt, IV-UMSC-PD-L1-HGF, IA-UMSC-PD-L1-Akt, IA-UMSC-PD-L1-HGF) have a better effect on the reduction of infarct size and the area of the largest infarction after a stroke than that of IV-UMSC-Akt, IA-UMSC-Akt, IV-UMSC-HGF, IA-UMSC-HGF, IV-UMSC-PD-L1, IA-UMSC-PD-L1, IV-UMSCs, IA-UMSCs and vehicle control by TTC stain (FIGS. 3A-B). Then, rats that received intracarotid combined with intravenous UMS C-PD-L1-Akt or UMS C-PD-L1-HGF (IA-IV-UMS C-PD-L1-Akt or IA-IV-UMS C-PD-L1-HGF) treatment showed mild infarction 3 days after cerebral ischemia by TTC examination (FIG. 3C). Quantitative measurement revealed that infarct volume was significantly reduced in IA-IV-UMSC-PD-L1-Akt-treated rats compared to IA-IV-UMSC-Akt-treated, IA-IV-UMSC-PD-L1-treated, IA-IV-UMSCs-treated and control animals (FIG. 3C). Consistently, the area of the largest infarction was smaller in IA-IV-UMSC-PD-L1-Akt treated rats than that in IA-IV-UMSC-Akt treated, IA-IV-UMSC-PD-L1 treated, IA-IV-UMSCs treated and control animals (FIG. 3C). Moreover, to further determine the neuroregenerative effect at 3 days after a stroke, a significant reduction of infarct volume and the largest infarcted slice were revealed in the IA-IV-UMSC-PD-L1-Akt or IA-IV-UMSC-PD-L1-HGF group over the IA-UMSC-PD-L1-Akt, IA-UMSC-PD-L1-HGF, IV-UMSC-PD-L1-Akt, IV-UMSC-PD-L1-HGF and control (FIG. 3D). In the meantime, similar (reproducible) results were also noted in the IA-IV-ADSC-PD-L1-Akt-treated or IA-IV-BMSC-PD-L1-Akt-treated rats (FIGS. 3E-F).

Figure 4A:
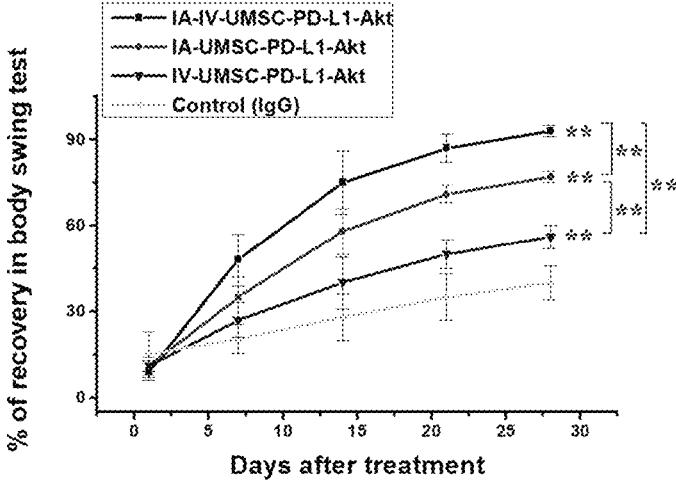
FIG. 4A shows the results of IA-IV-UMSC-PD-L1-Akt, IA-UMSC-PD-L1-Akt, IV-UMSC-PD-L1-Akt and control group treatments in the body swing test.
Figure 4B:
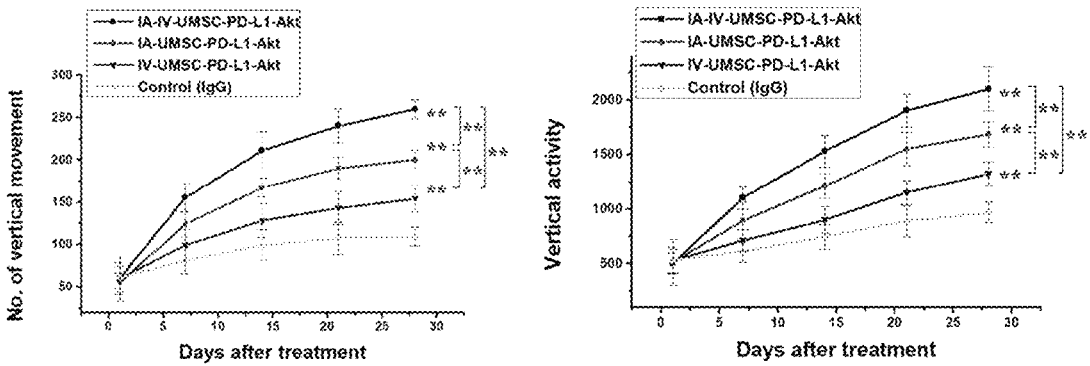
FIG. 4B shows the results of IA-IV-UMSC-PD-L1-Akt, IA-UMSC-PD-L1-Akt, IV-UMSC-PD-L1-Akt and control group treatments in the vertical movement test.
Figure 4B:
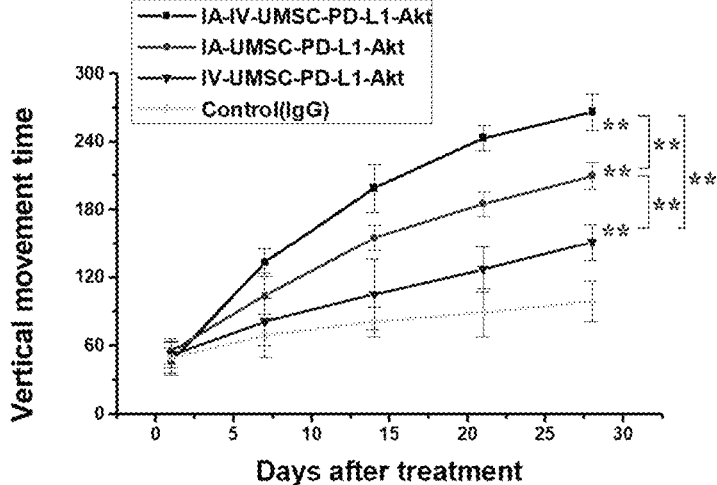
Figure 4C:
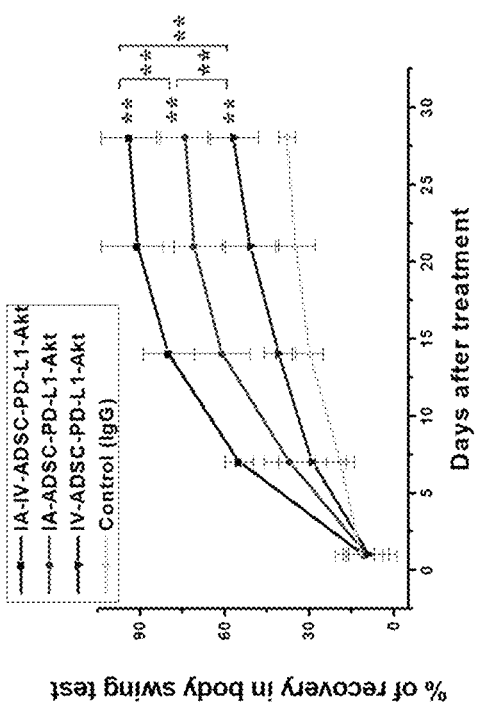
FIG. 4C shows the results of IA-IV-ADSC-PD-L1-Akt, IA-ADSC-PD-L1-Akt, IV-ADSC-PD-L1-Akt and control group treatments in the vertical movement test.
Figure 4C:
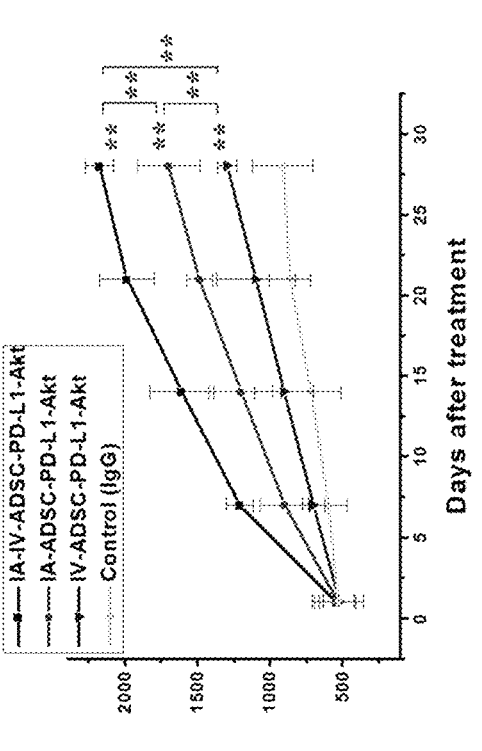
Figure 4C:
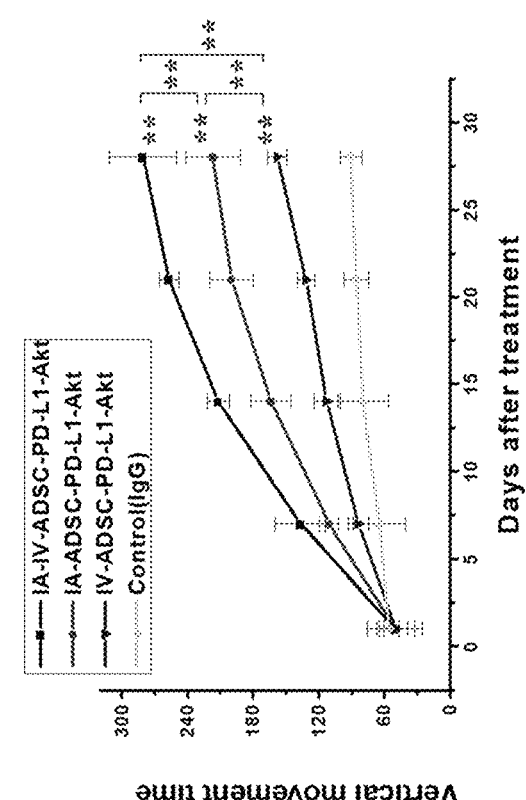
Figure 4D:
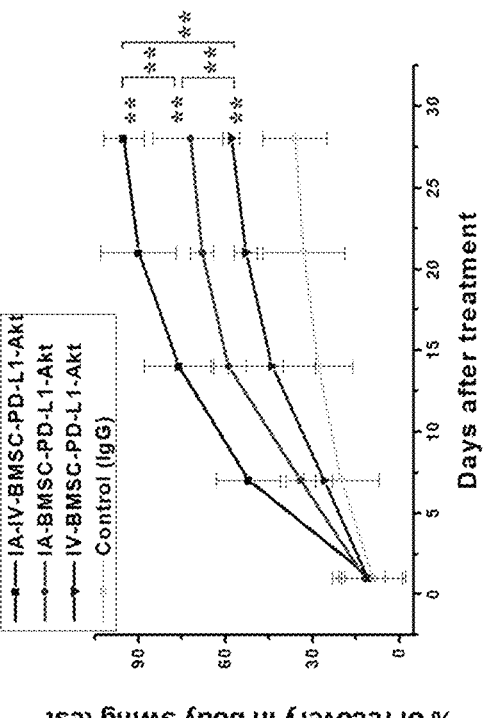
FIG. 4D shows the results of IA-IV-BMSC-PD-L1-Akt, IA-BMSC-PD-L1-Akt, IV-BMSC-PD-L1-Akt and control group treatments in the vertical movement test.
Figure 4D:
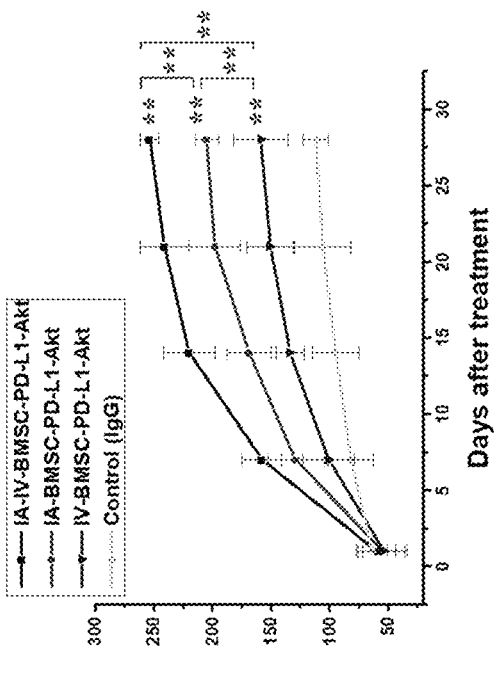
Figure 4D:
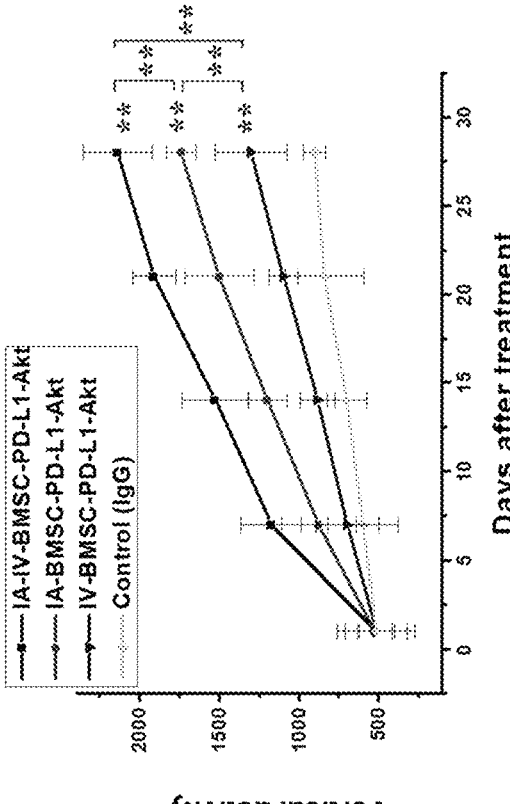
Figure 4D:
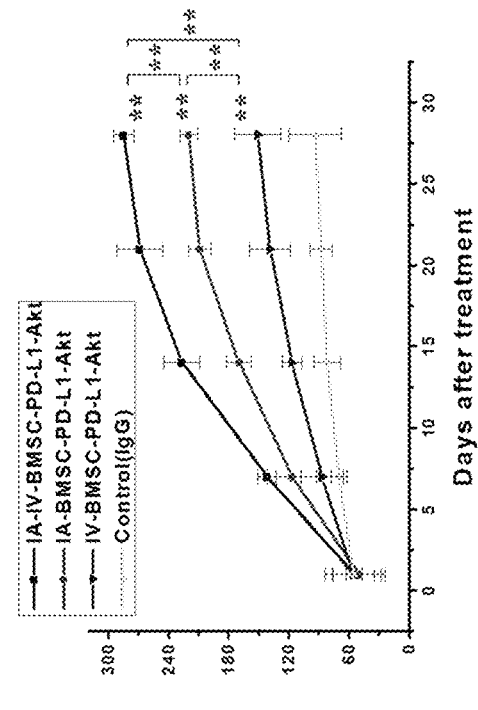

Example 5 Intracarotid Combined with Intravenous UMSC-PD-L1-Akt, ADSC-PD-L1-Akt or BMSC-PD-L1-Akt Transplantation Improved Neurological Behavior in Stroke Rats In vivo neuroregenerative potential of IA-IV-UMSC-PD-L1-Akt was demonstrated in a stroke model. Two modalities of a neurological deficit measurement (body asymmetry and locomotor activity) were evaluated before and after strokes in rats for 28 days. First, we subdivided rats into four treatment groups, including IA-IV-UMSC-PD-L1-Akt, IA-UMSC-PD-L1-Akt, IV-UMSC-PD-L1-Akt, and a control group to evaluate the recovery behavior in stroke rats. Better recovery was found in IA-IV-UMSC-PD-L1-Akt treated rats than in that of IA-UMSC-PD-L1-Akt, IV-UM-SCt-PD-L1-Akt and control group in the body asymmetry assay (FIG. 4A). Moreover, significant improvement of neurological deficit was also observed in the IA-IV-UMSC-PD-L1-Akt treated rats compared to that of IA-UMSC-PD-L1-Akt, IV-UMSC-PD-L1-Akt and control group (FIG. 4B). These results suggest that IA-IV-UMSC-PD-L1-Akt have superior neuroregenerative potential for strokes. Consistently, similar (reproducible) results were also noted in the IA-IV-ADSC-PD-L1-Akt-treated or IA-IV-BMSC-PD-L1-Akt-treated rats (FIGS. 4C-D).

Figure 4E:
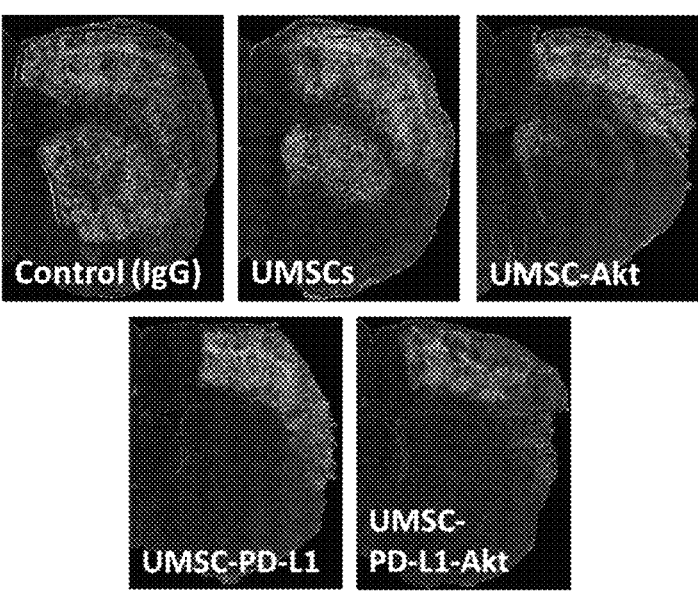
FIG. 4E shows the results of neuronal death in rats treated with IA-IV-UMSC-PD-L1-Akt, IA-UMSC-PD-L1-Akt, IV-UMSC-PD-L1-Akt, and control group.
Figure 4E:
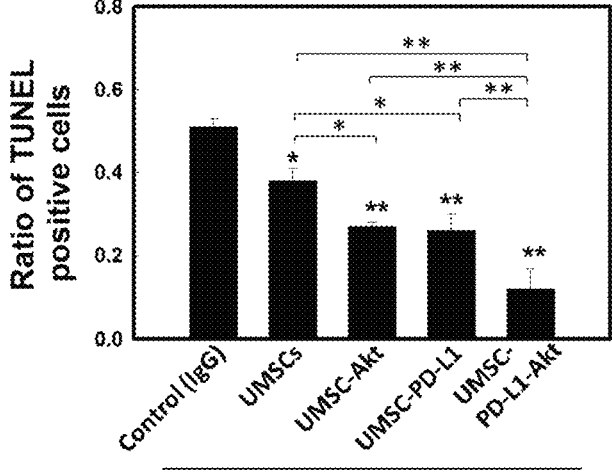

Example 6 UMSC-PD-L1-Akt Treatment Reduced the Neuronal Death from Stroke Brain Damage Cellular apoptosis in the ischemic rat brain was studied by TUNEL staining. Control animals without strokes had almost no TUNEL staining in any section of their brain. The penumbral region surrounding the ischemic cores of IA-IV-UMSC-PD-L1-Akt-treated rats contained fewer TUNEL$^+$ cells than that of IA-IV-UMSC, IA-IV-UMSC-Akt, IA-IV-UMSC-PD-L1 and control group (FIG. 4E).

Example 7 Targeting of UMSC-PD-L1-Akt-Luc in the Stroke Model

Figure 5A:
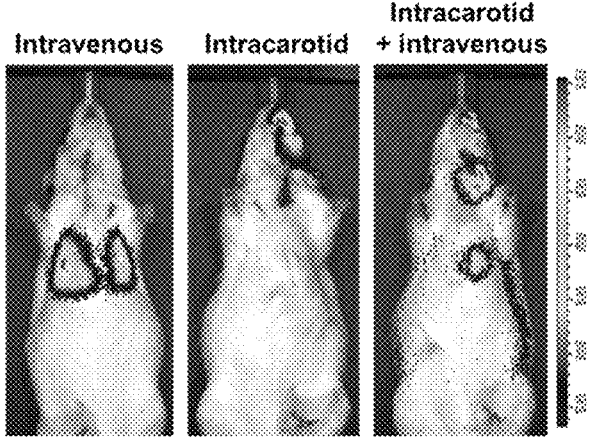
FIG. 5A shows the IVIS results of biodistribution of after intravenous, intracarotid and combined intravenous and intracarotid injections of UMSC-PD-L1-Akt-Luc.
Figures 5B, 5C:
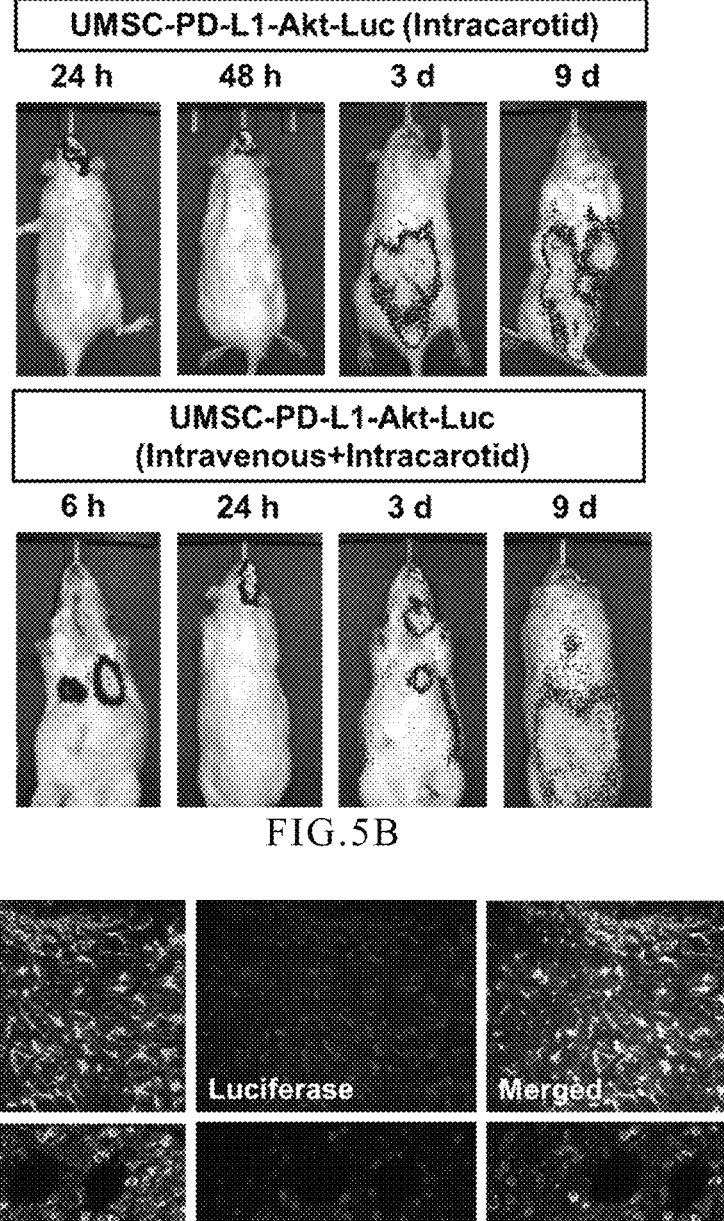
FIG. 5B shows the IVIS results of biodistribution at different time points after intravenous, intracarotid and combined intravenous and intracarotid injections of UMSC-PD-L1-Akt-Luc.
FIG. 5C shows the confocal microscope immunofluorescence results of combined intravenous and intracarotid injection of UMSC-PD-L1-Akt-Luc.

To demonstrate the UMSC-PD-L1-Akt homing effect, biodistribution of UMSC-PD-L1-Akt-Luc after intracarotid or intravenous implantation was performed using IVIS. Intravenous UMSC-PD-L1-Akt-Luc transplantation was initially entrapped in the lung capillary from 6 hours after injection, which showed enhanced bioluminescent image of IVIS in lungs (FIG. 5A). With respect to the intracarotid injection at 24 hours after stroke, homing of UMSC-PD-L1-Akt-Luc did survive and relocate into the right cerebral hemisphere of the stroke area without lung uptake from 6 hours to over one week (FIG. 5B). In IA-IV-UMSC-PD-L1-Akt-Luc group, biodistribution of the UMSC-PD-L1-Akt-Luc was tracked both in the right hemisphere and lungs from 6 hours to over one week (FIG. 5B). Moreover, luciferase$^+$ cells homed into the peri-infarcted area revealed colocalization with either neuronal marker of MAP-2 or glial marker of GFAP in the immunofluorescent study by confocal microscopy (FIG. 5C).

Figures 1, 6A:
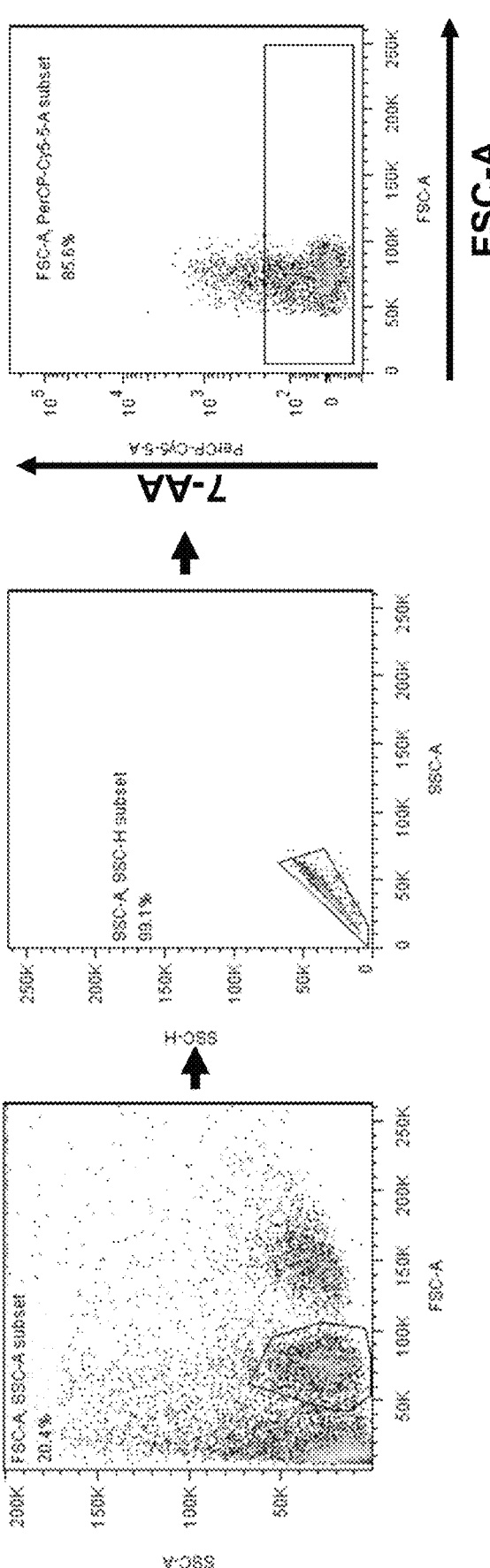
FIGS. 6A-1 and 6A-2 show the gating strategy of IA-IV-UMSC-PD-L1-Akt for analyzing inflammatory cells in the cerebral hemisphere by flow cytometry.
Figures 1, 6A:
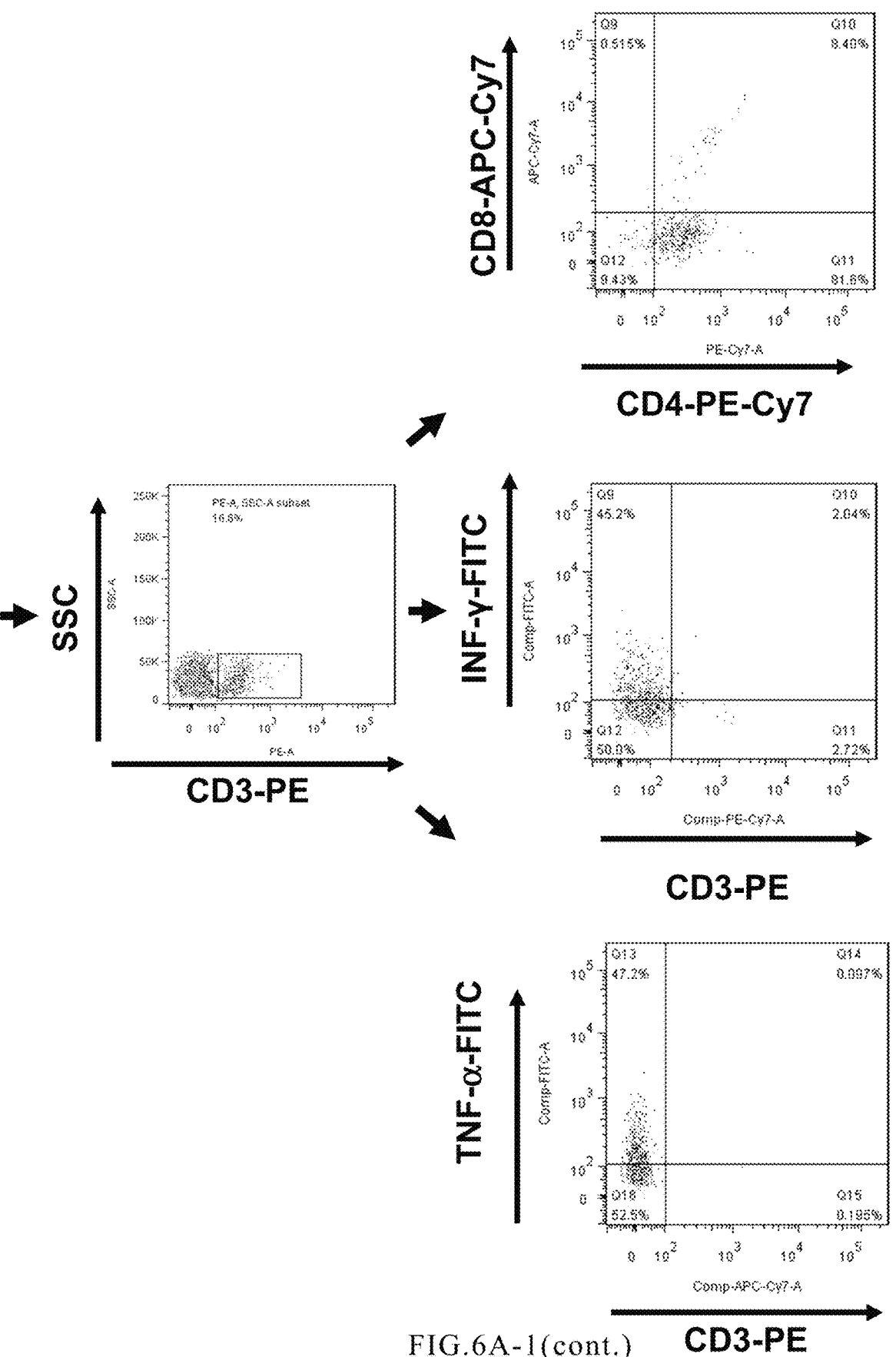
Figures 2, 6A:
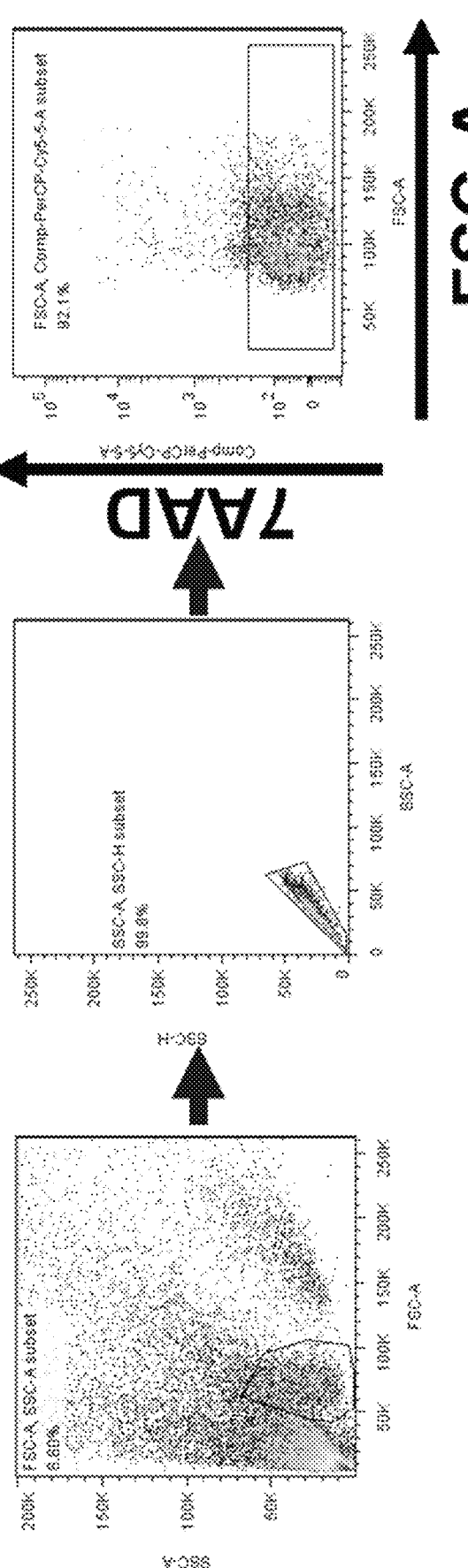
Figures 2, 6A:
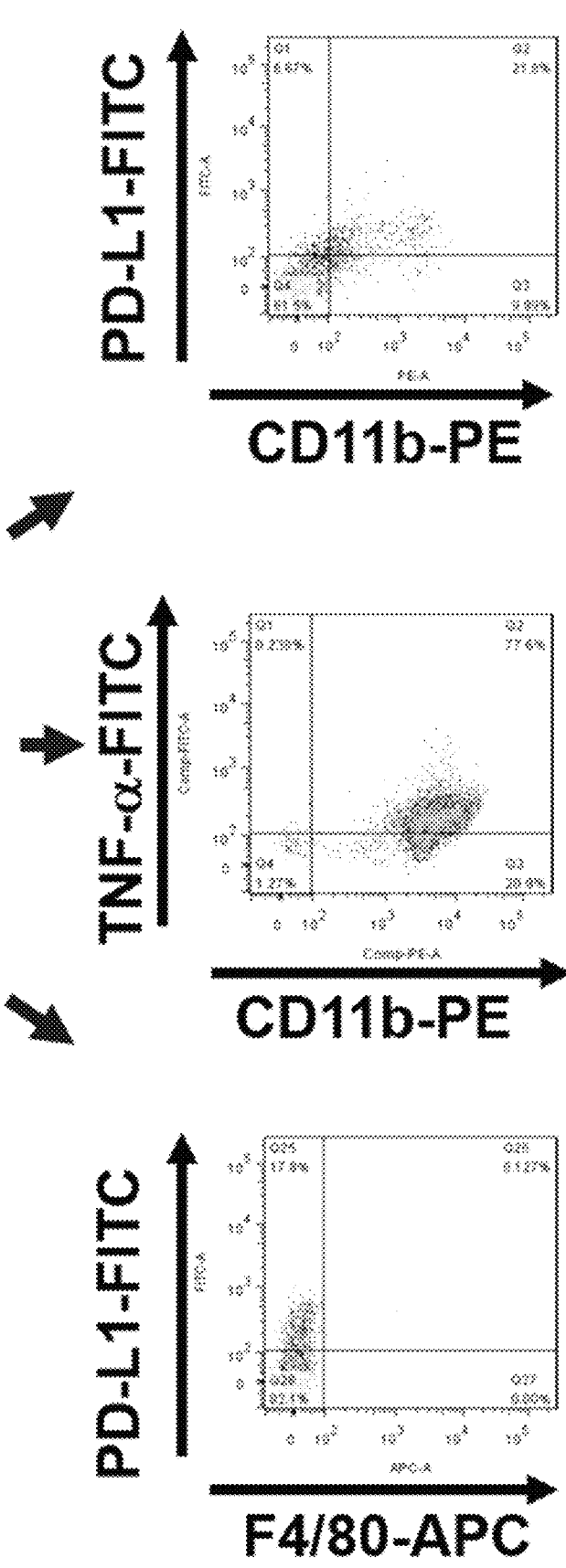
Figure 6B:
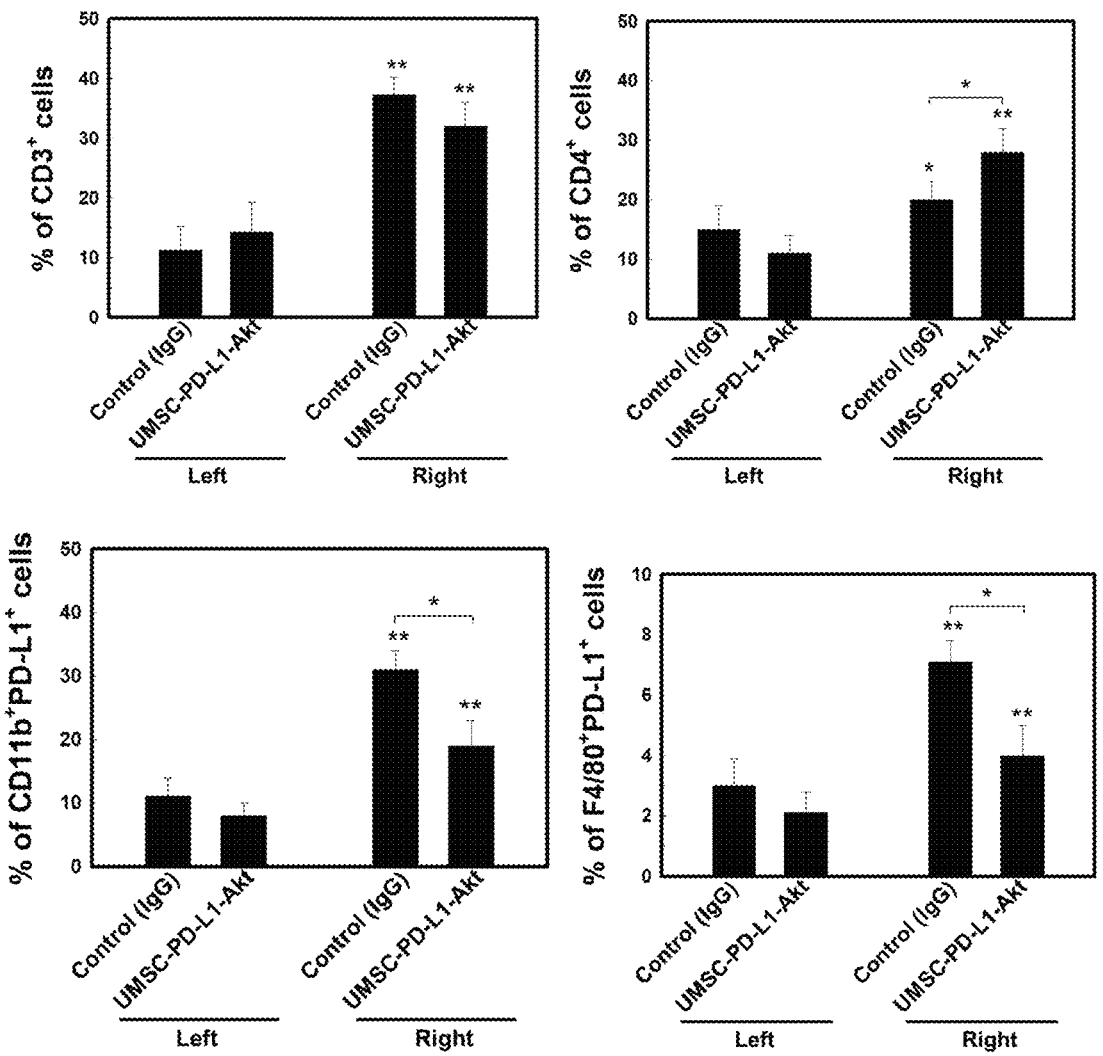
FIG. 6B shows the results of flow cytometry analysis of $CD3^+$ T cells, $CD4^+$ T cells, $CD11b^+PD-L1^+$ macrophages and $F4/80^+PD-L1^+$ microglia after IA-IV-UMSC-PD-L1-Akt treatment.
Figure 6C:
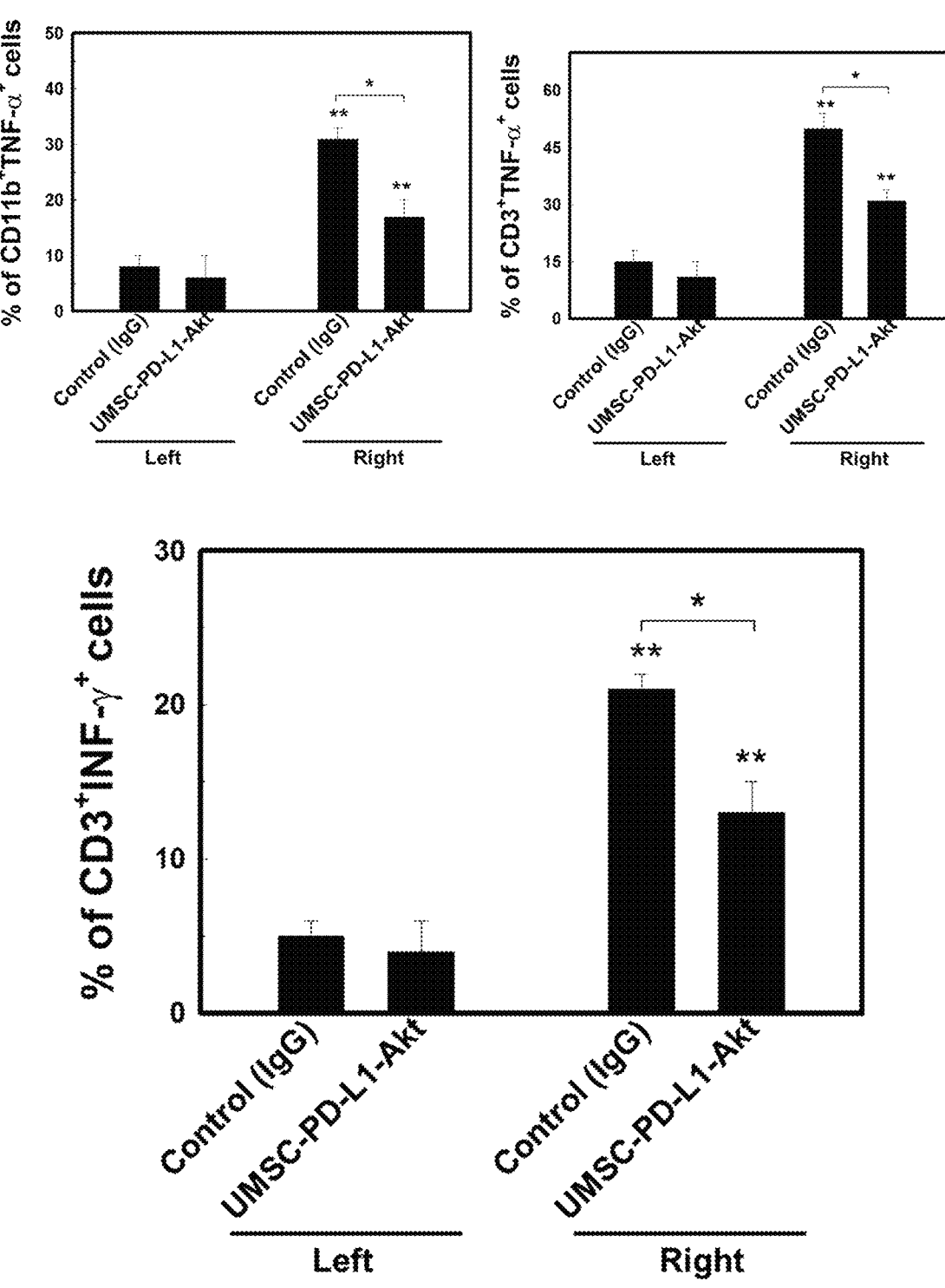
FIG. 6C shows the results of flow cytometry analysis of $CD11b^+TNF-\alpha^+$, $CD3^+TNF-\alpha^+$ and $CD3^+INF-\gamma^+$ cells in the cerebral hemisphere after IA-IV-UMSC-PD-L1-Akt treatment.
Figures 1, 6D:
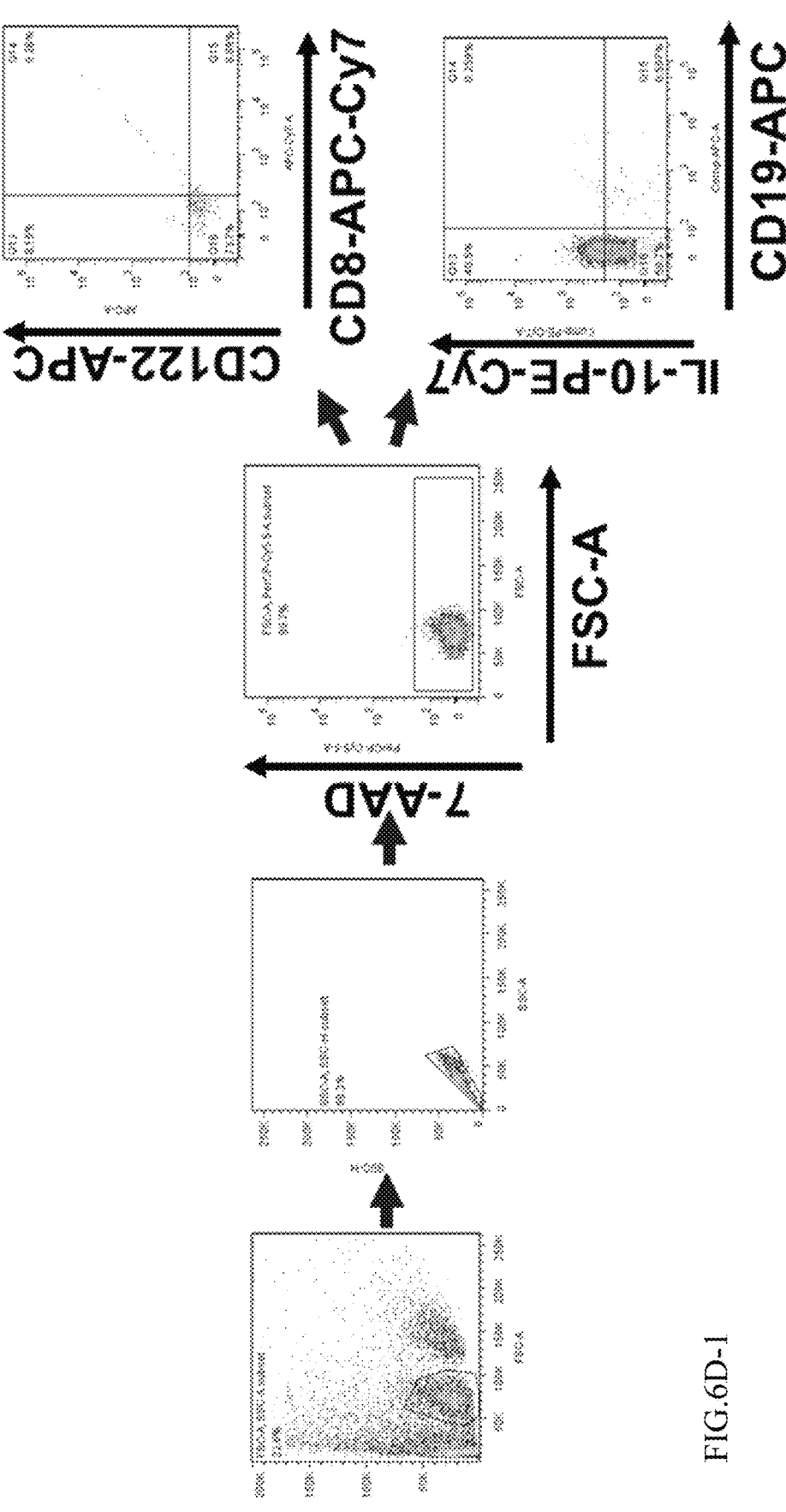
Figures 2, 6D:
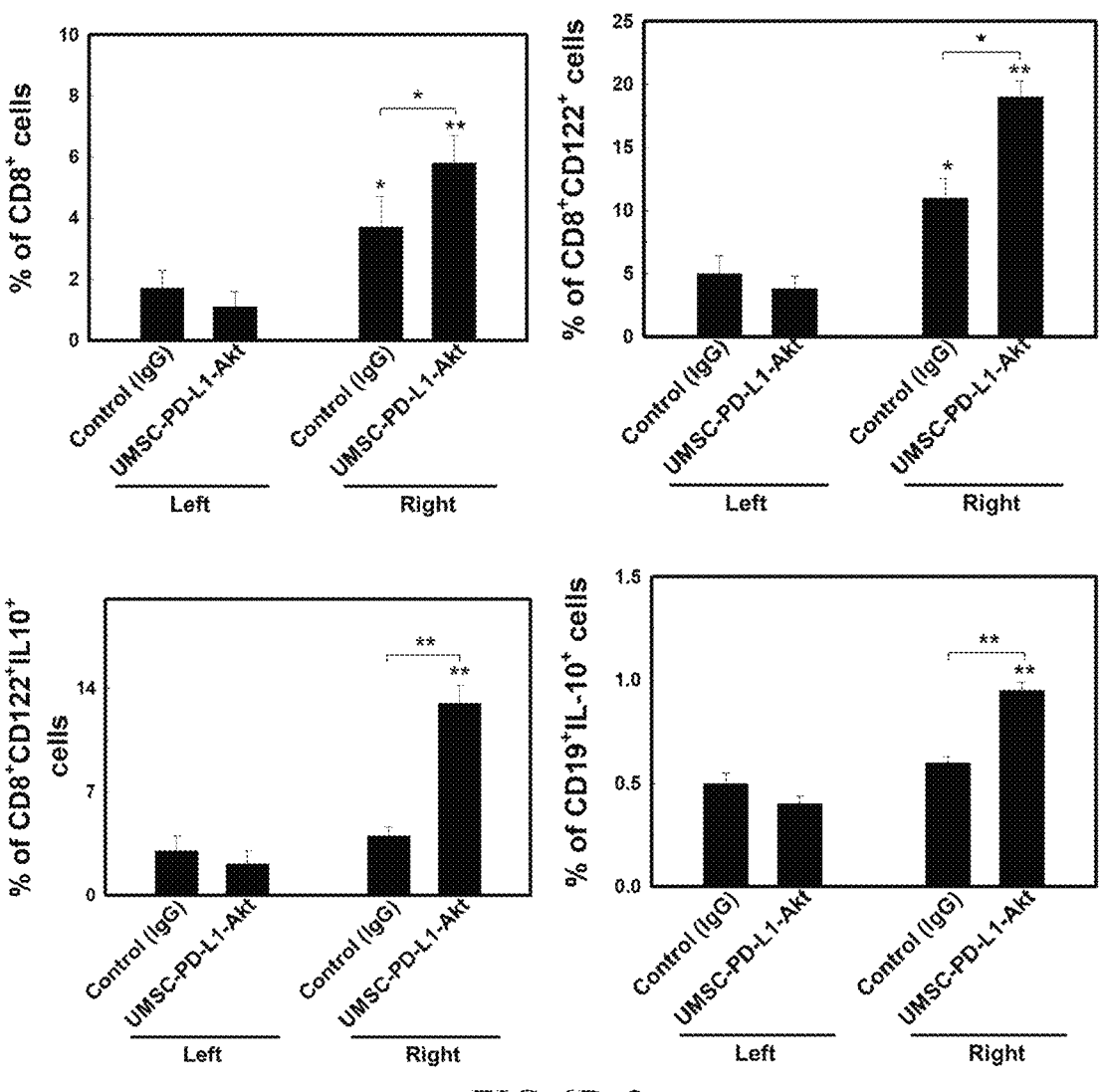

Example 8 IA-IV-UMSC-PD-L1-Akt Treatment Reduces Inflammatory Responses but Enhances Accumulation of CD8$^+$CD122$^+$ Tregs in the Ischemic Brain To demonstrate if UMSC-PD-L1-Akt altered leukocyte composition in brain after a stroke, absolute numbers of total viable leukocytes were examined. The gating strategy was performed and depicted as a uniform procedure (FIG. 6A). The ischemic hemisphere in rats treated with UMSC-PD-L1-Akt had a significant increase in the total number of viable leukocytes including CD3$^+$ T cells, CD4$^+$ T cell, CD11b$^+$PD-L1$^+$ macrophage and F4/80$^+$PD-L1$^+$ microglia compared with the unaffected hemisphere, while the total cell numbers did not change between treatment and control groups in either hemisphere (FIG. 6B). UMSC-PD-L1-Akt treatment in stroke rats significantly reduced the percentage of activated CD11b$^+$tumor necrosis factor-$\alpha$ (TNF-$\alpha$)$^+$, CD11b$^+$INF-$\gamma^+$, CD3$^+$TNF-$\alpha^+$ and CD3$^+$INF-$\gamma^+$ cells (FIG. 6C), which enhanced the percentages of total CD8$^+$, CD8$^+$CD122$^+$IL-10$^+$ Treg cells and CD19$^+$IL-10$^+$ Breg cells (FIG. 6D) in the ischemic hemisphere, with a corresponding increase in IL-10 production. No effects of anti-PD-L1 mAb treatment of MCAO mice were observed on CNS infiltrating CD4$^+$ T cells, although a nominal reduction in CD5$^+$CD1dhi CD19$^+$ Breg cells was observed.

Figures 1, 7A:
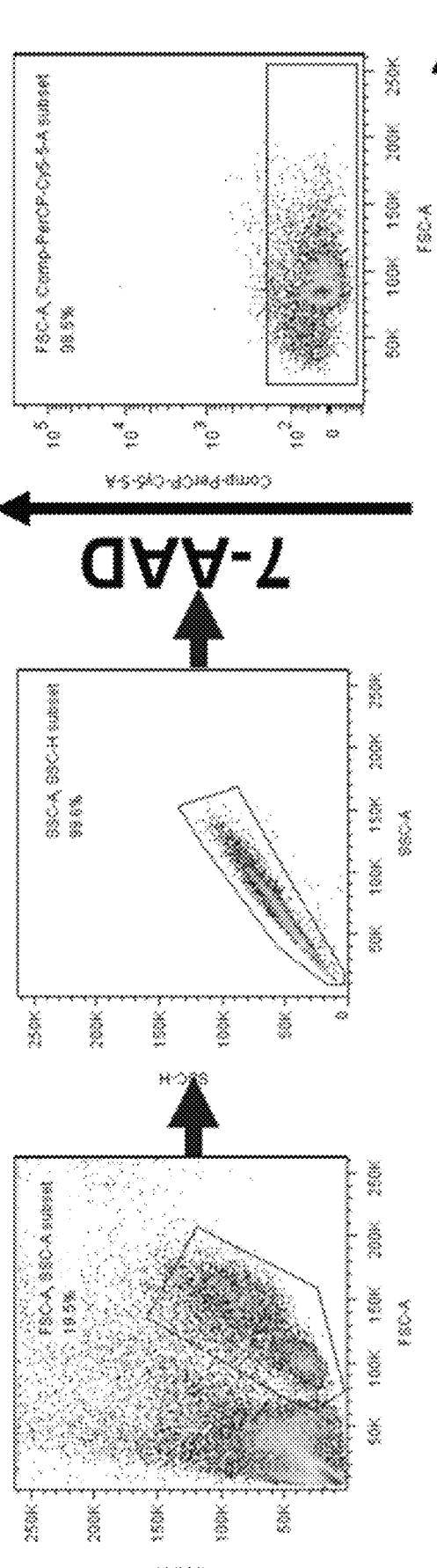
Figures 1, 7A:
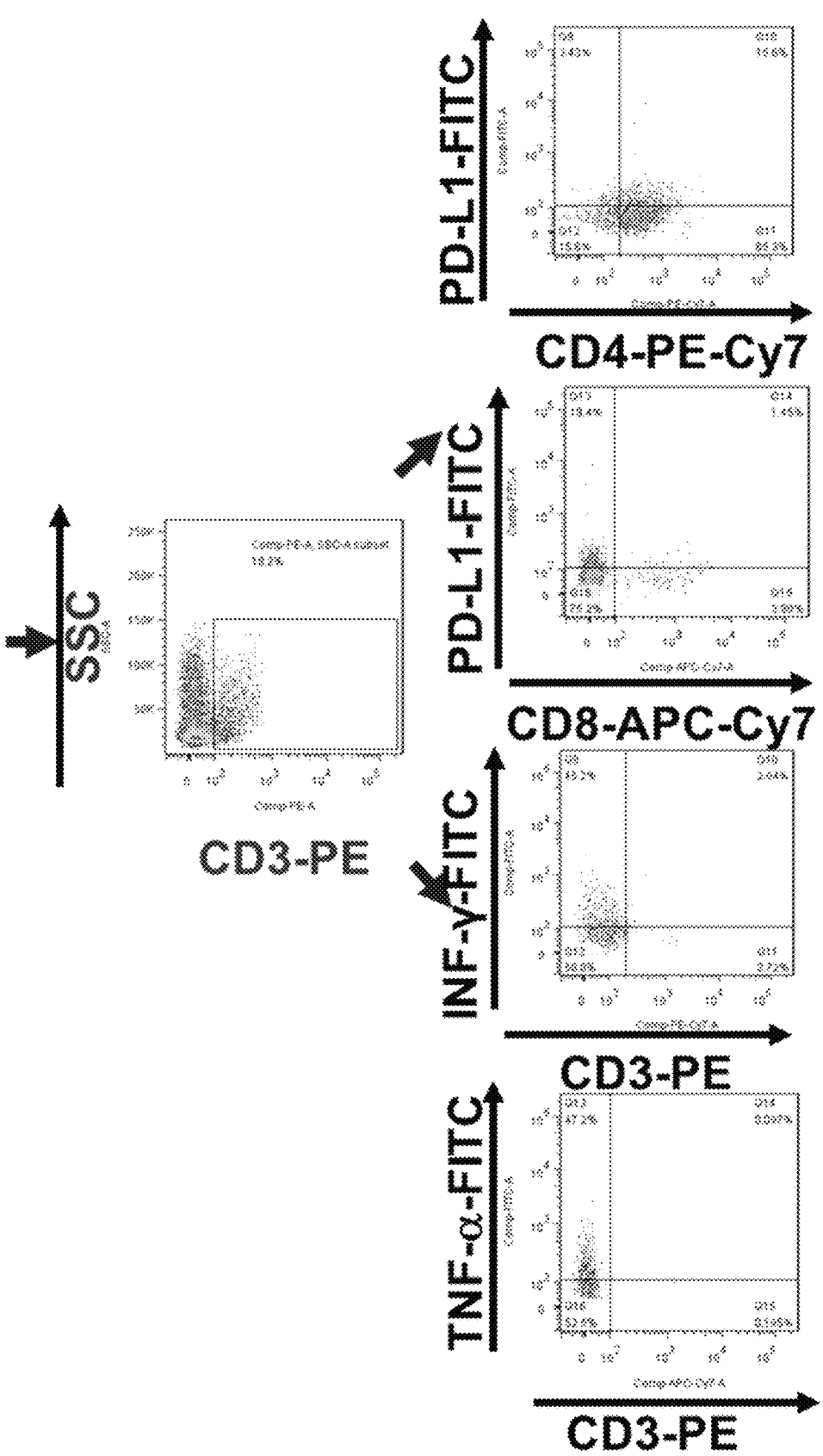
Figures 2, 7A:
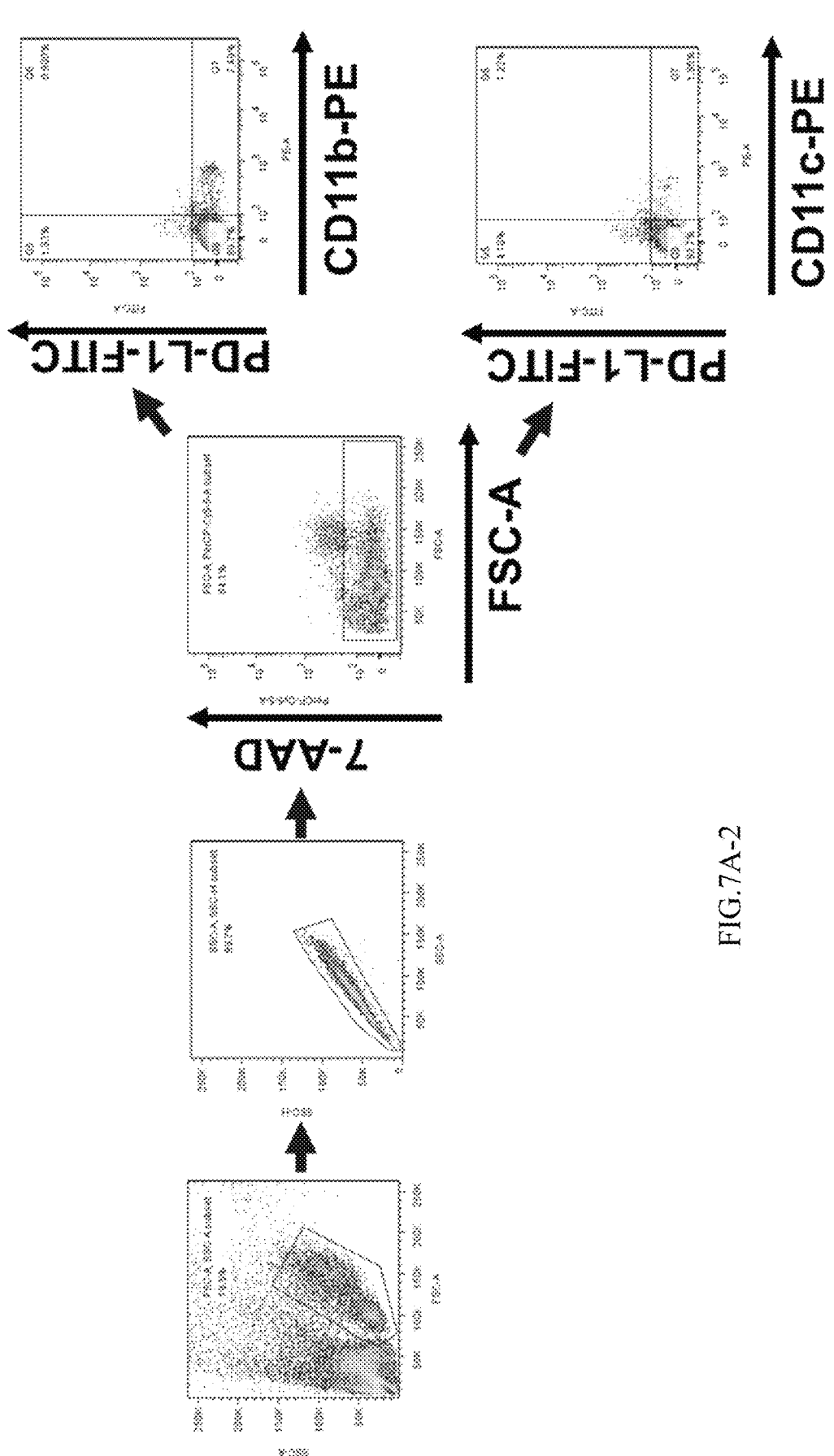
Figures 3, 7A:
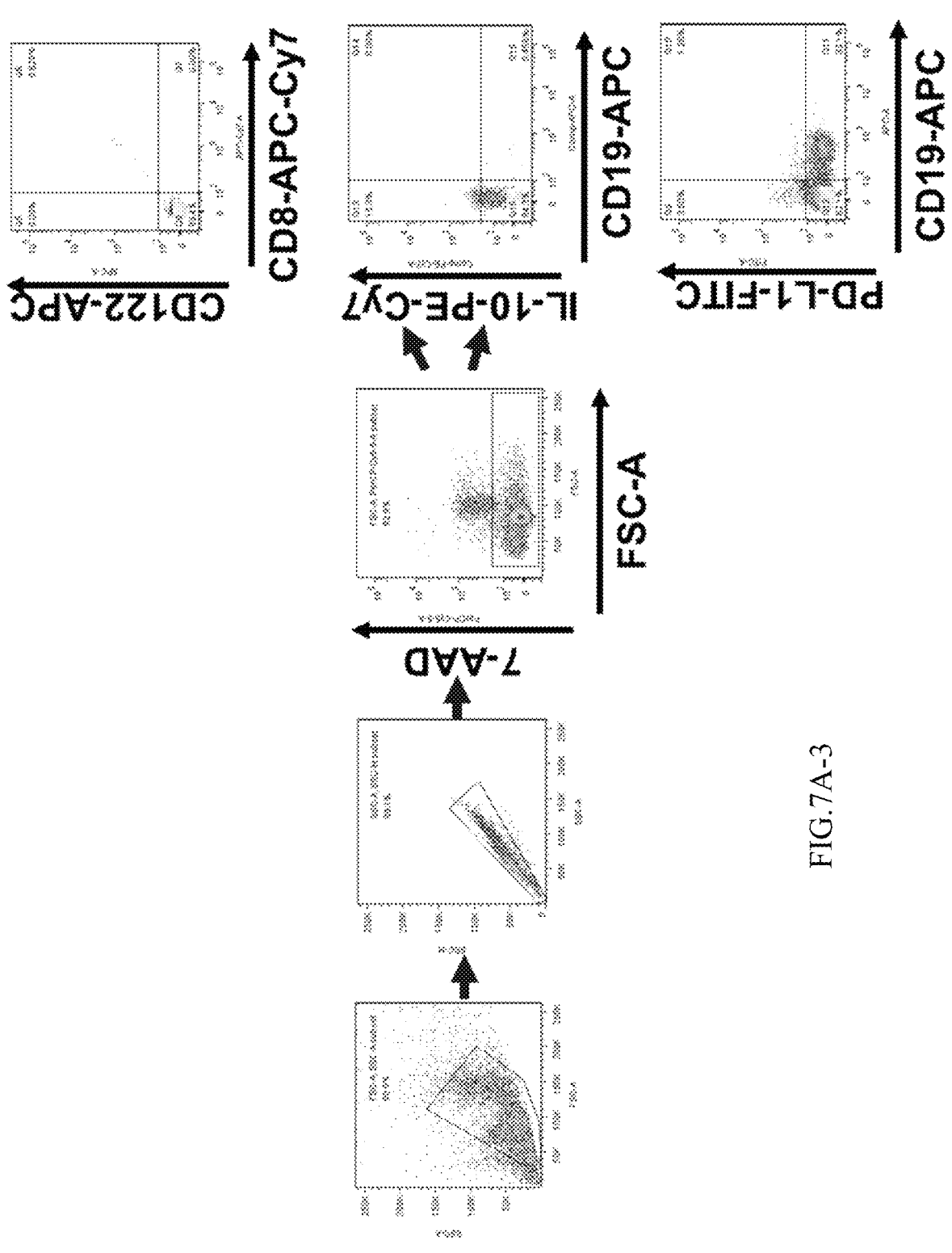
Figures 4, 7A:
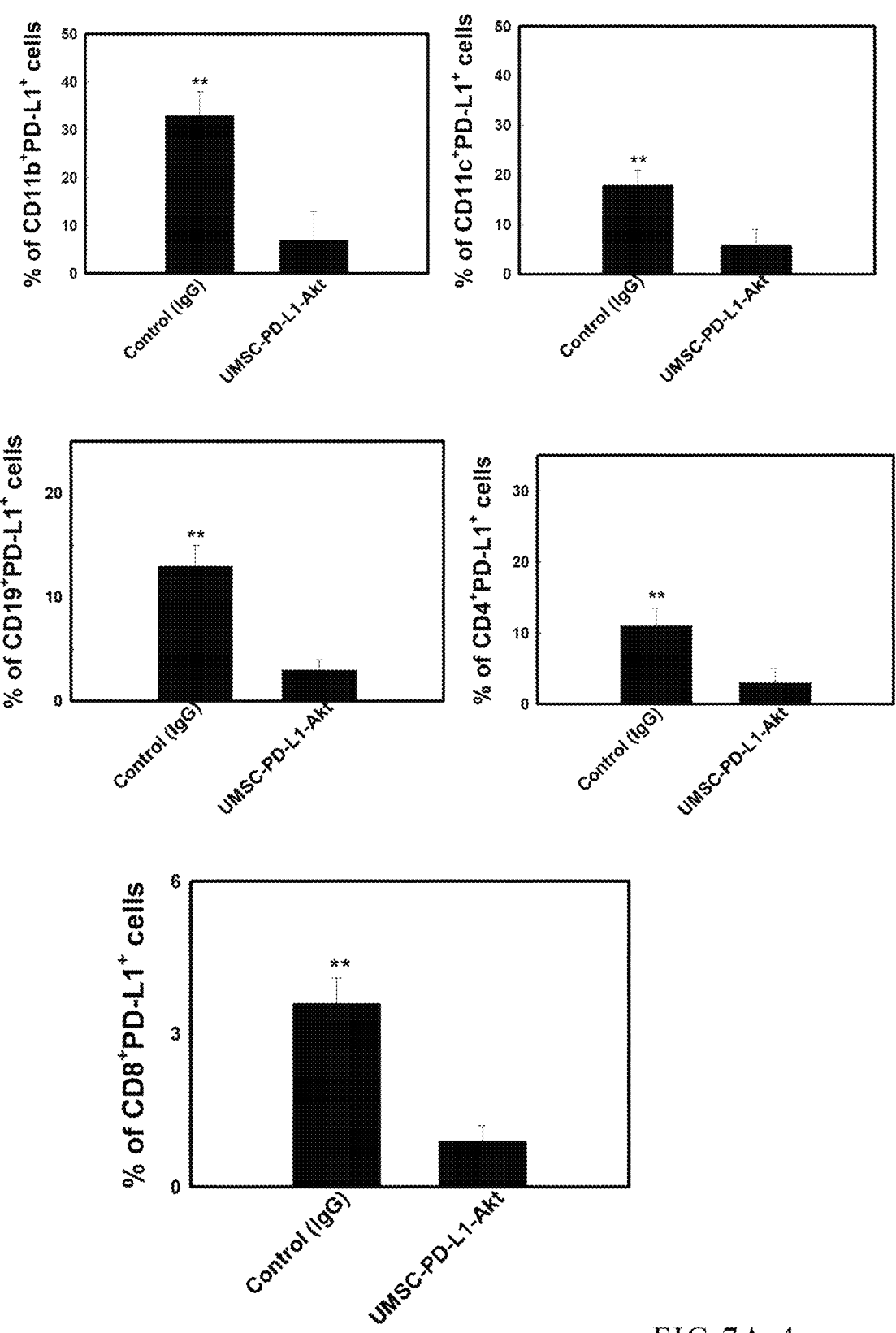
Figures 7B, 7C:
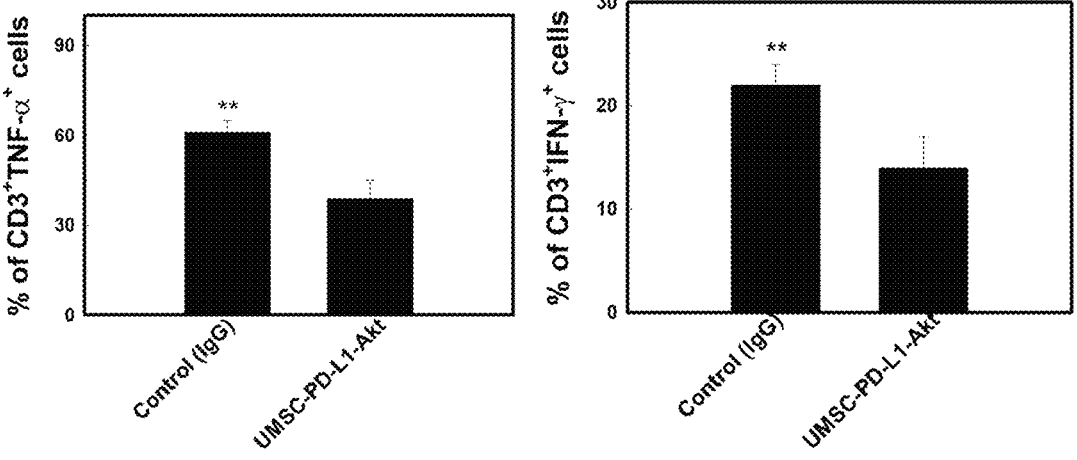
FIG. 7B shows the results of flow cytometry analysis of $CD3^+TNF-=^+$ and $CD3^+INF-\gamma^+$ cells of spleen cells treated with UMSC-PD-L1-Akt.
FIG. 7C shows the results of flow cytometry analysis of $CD8^+CD122^+$ and $CD19^+IL-10^+$ cells of spleen cells treated with UMSC-PD-L1-Akt.

Example 9 IA-IV-UMSC-PD-L1-Akt Treatment Increases the Expression of Regulatory Molecules on T Cells in Spleens After Stroke To evaluate on peripheral immunity after UMSC-PD-L1-Akt treatment, flow cytometry analysis was performed for the spleen in stroke animals. Treatment with UMSC-PD-L1-Akt at 4 hours after a stroke strongly inhibited expression of PD-L1 on CD19$^+$ B cells, CD4$^+$ and CD8$^+$ T cells, CD11b$^+$ monocytes/macrophages, and CD11c$^+$ dendritic cells (DCs) in the spleens assessed after 96 hours of stroke (FIG. 7A-4). In contrast, UMSC-PD-L1-Akt significantly reduced the percentage of activated CD3$^+$TNF-$\alpha^+$ and CD3$^+$ INF-$\gamma^+$ inflammatory cells in the spleen (FIG. 7B). Moreover, an increased percentage of CD8$^+$CD122$^+$ Tregs and CD19$^+$IL-10$^+$ Bregs (FIG. 7C) in the spleen was observed in UMSC-PD-L1-Akt-treated stroke mice. There were no changes in the frequency of Foxp3$^+$CD4$^+$CD25$^+$ Tregs after UMSC-PD-L1-Akt, suggesting the lack of involvement in the PD-1/PD-L pathway for the generation of this Treg subpopulation.

Figure 8A:
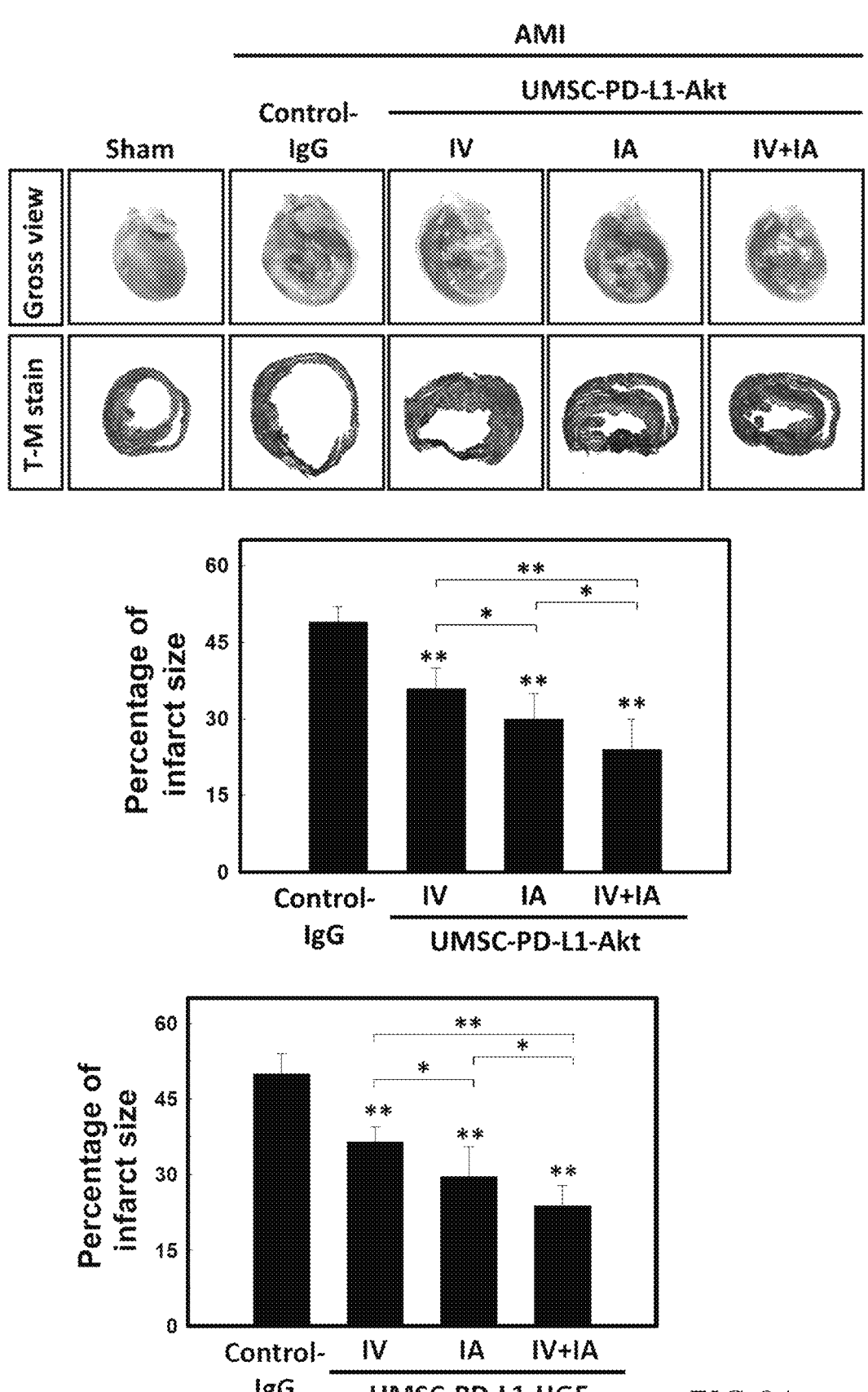
FIG. 8A shows the results of infarct area in AMI model in intravenous (IV), intracarotid (IA) and combined intravenous and intracarotid (IV+IA) injections of UMSC-PD-L1-Akt or UMSC-PD-L1-HGF.
Figure 8B:
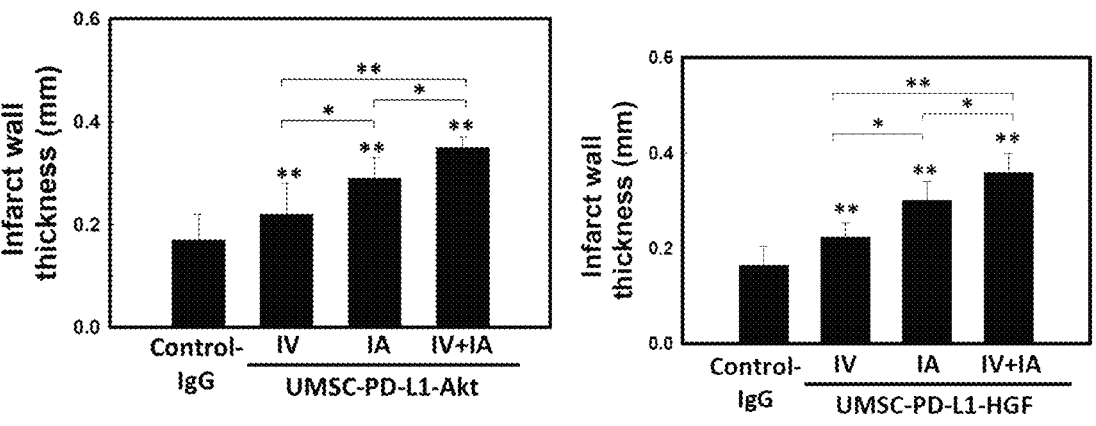
FIG. 8B shows the results of infarct wall thickness in AMI model in intravenous (IV), intracarotid (IA) and combined intravenous and intracarotid (IV+IA) injections of UMSC-PD-L1-Akt or UMSC-PD-L1-HGF.
Figure 8C:
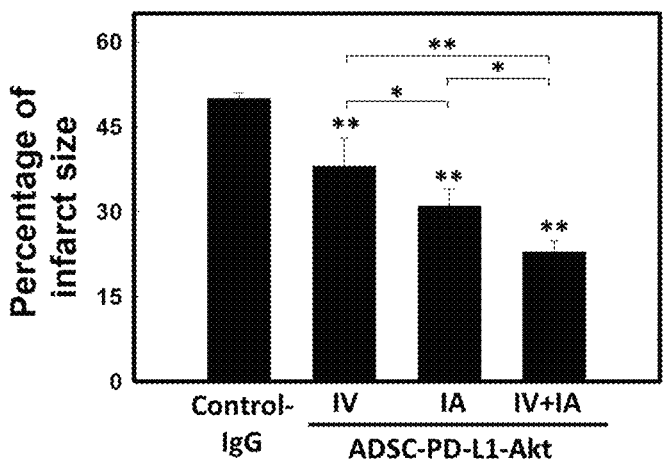
FIG. 8C shows the results of infarct area and infarct wall thickness in AMI model in intravenous (IV), intracarotid (IA) and combined intravenous and intracarotid (IV+IA) injections of ADSC-PD-L1-Akt.
Figure 8C:
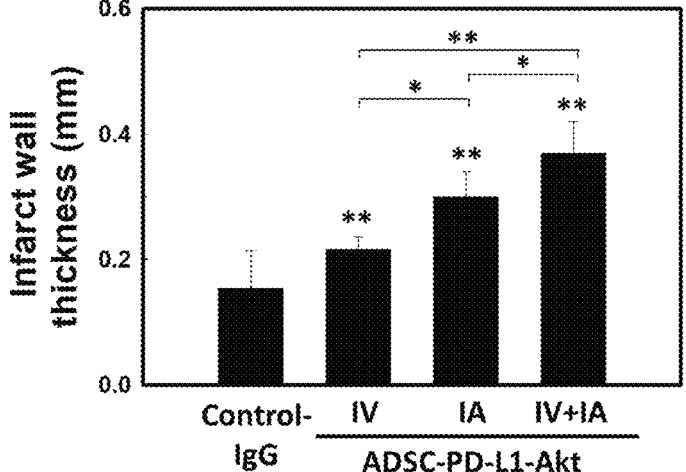
Figure 8D:
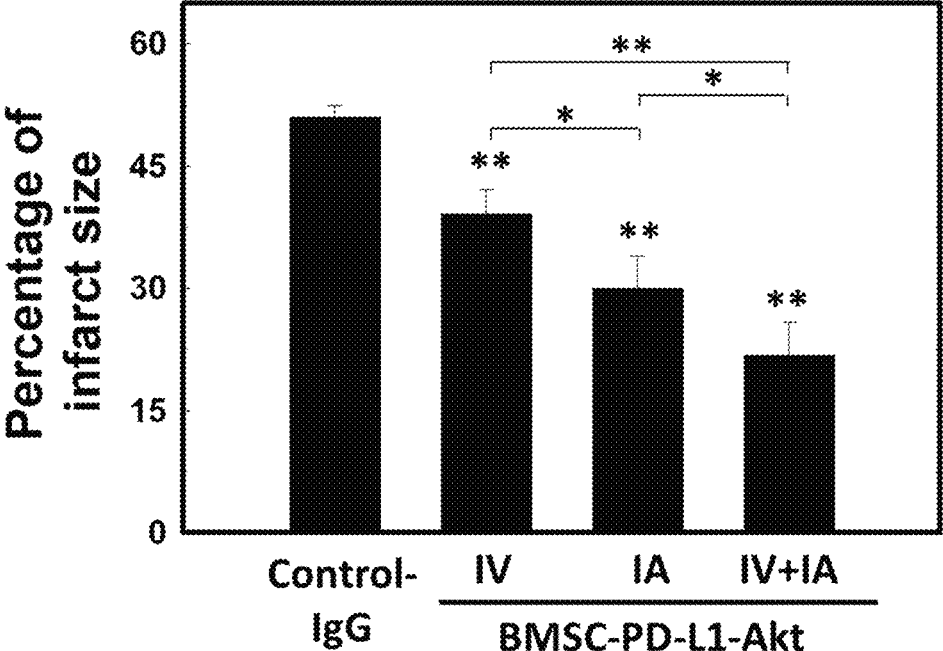
FIG. 8D shows the results of infarct area and infarct wall thickness in AMI model in intravenous (IV), intracarotid (IA) and combined intravenous and intracarotid (IV+IA) injections of BMSC-PD-L1-Akt.

Example 10 Attenuation of Post-MI LV Dysfunction and Reduced Infarct Size After MI Through Intra-Carotid Combined with Intravenous Administration of UMSC-PD-L1-Akt, UMSC-PD-L1-HGF, ADSC-PD-L1-Akt or BMSC-PD-L1-Akt To verify whether either intravenous (IV) or intraarterial (IA) UMSC-PD-L1-Akt or UMSC-PD-L1-HGF, (IV-UMSC-PD-L1-Akt, IV-UMSC-PD-L1-HGF, IA-UMSC-PD-L1-Akt, IA-UMSC-PD-L1-HGF, IV-IA-UMSC-PD-L1-Akt or IV-IA-UMSC-PD-L1-HGF) play a significant role in rescuing the heart from ischemic injury, we examined the infarct size in the AMI model. The infarct volume of the IV-IA-UMSC-PD-L1-Akt-treated or IV-IA-UMSC-PD-L1-HGF-treated group at 28 days post-MI was much smaller than the infarct volumes in IV-UMSC-PD-L1-Akt, IV-UMSC-PD-L1-HGF, IA-UMSC-PD-L1-Akt, IA-UMSC-PD-L1-HGF and control group (FIG. 8A). In addition, IV-IA-UMSC-PD-L1-Akt-treated or IV-IA-UMSC-PD-L1-HGF-treated group increased the thickness of the infarct wall as compared to a thin wall in control group (FIG. 2B). In the meantime, similar (reproducible) results were also noted in the IV-IA-ADSC-PD-L1-Akt-treated or IV-IA-BMSC-PD-L1-Akt-treated rats (FIGS. 8C-D).

Example 11 Anti-Inflammatory Effect of
UMSC-PD-L1-Akt on Ischemic Myocardium

Figure 9A:
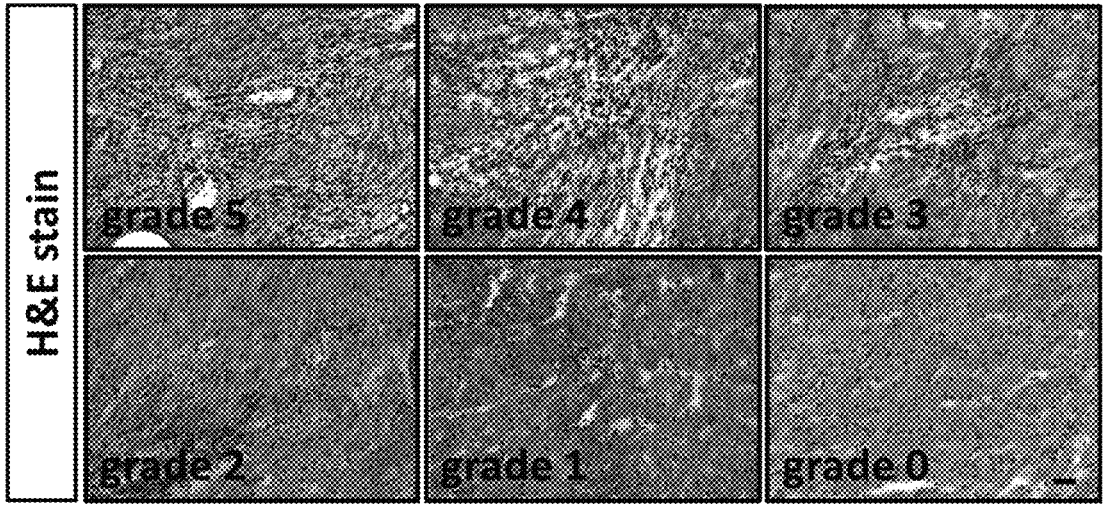
FIG. 9A shows the results of the grade of inflammation in intravenous (IV), intracarotid (IA) and combined intravenous and intracarotid (IV+IA) injections of UMSC-PD-L1-Akt.
Figure 9A:
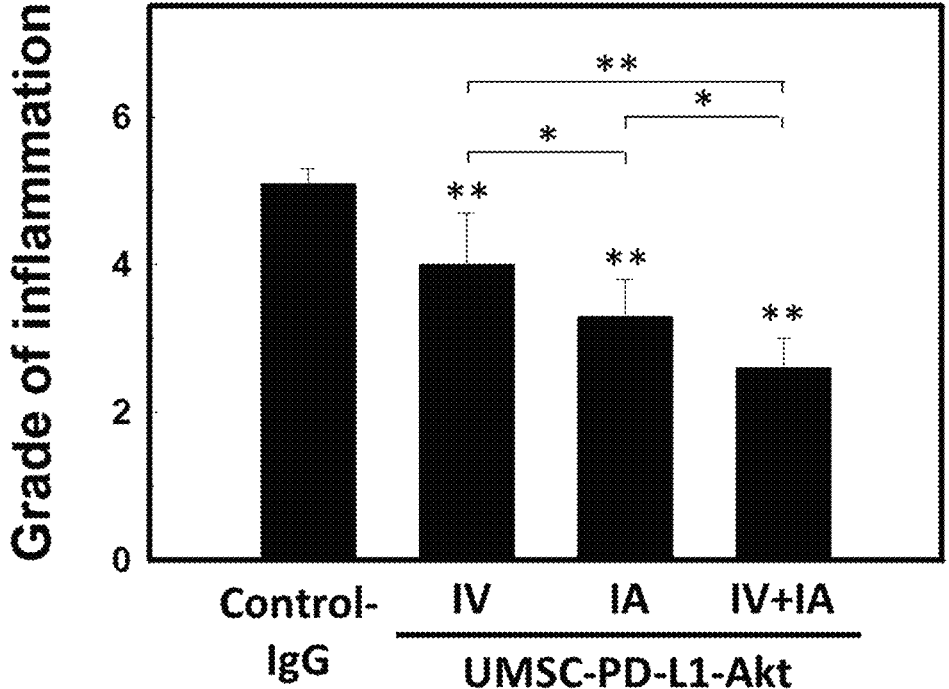
Figure 9B:
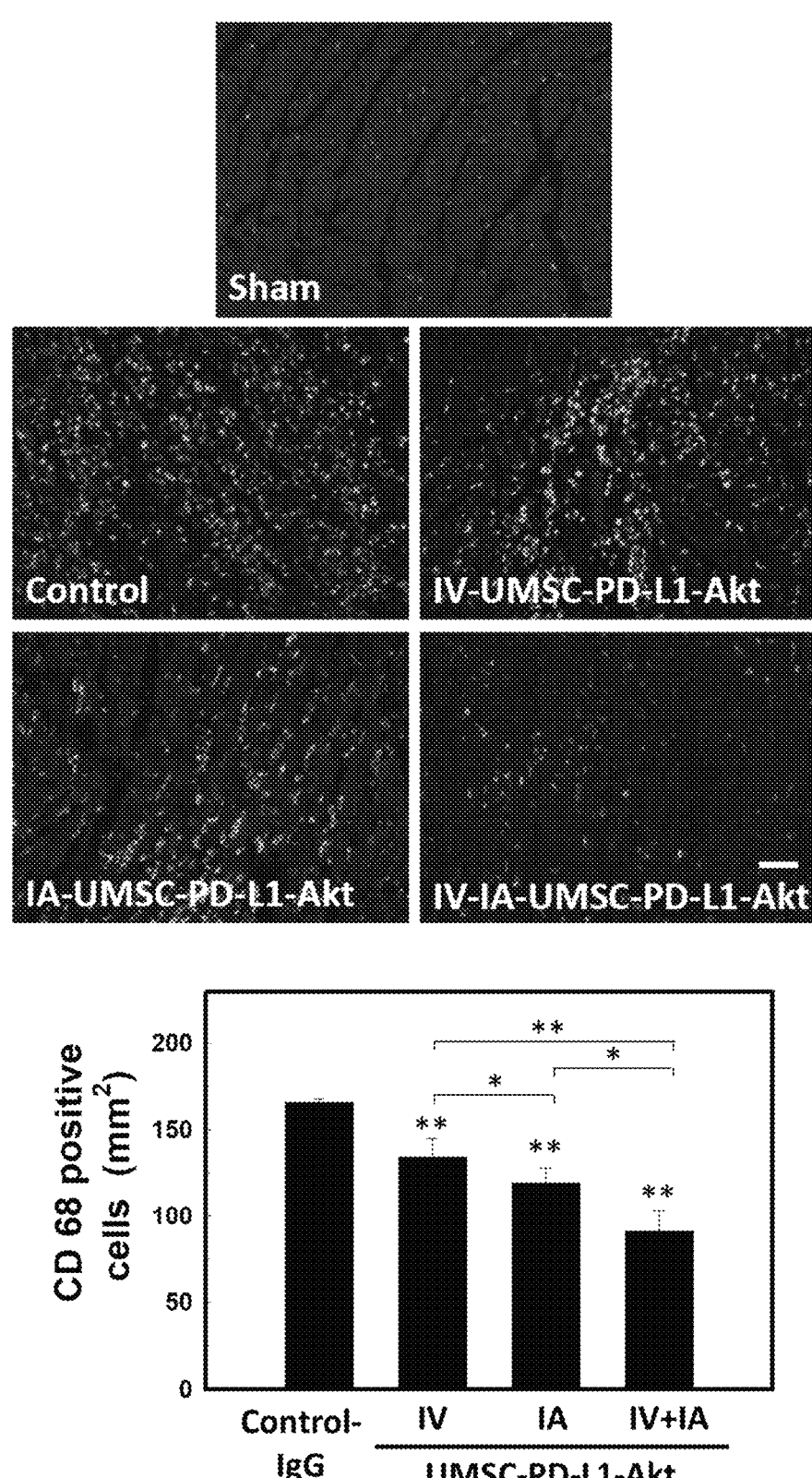
FIG. 9B shows the results of CD68+ infiltration after three days of MI in intravenous (IV), intracarotid (IA) and combined intravenous and intracarotid (IV+IA) injections of UMSC-PD-L1-Akt.

To examine whether UMSC-Akt-PD-L1 treatment suppressed inflammatory response post-MI, we performed immunohistochemical analysis for studying the inflammatory cell infiltration on 3 days post-MI. Significant reduction of inflammation was observed in the IV-IA-UMSC-PD-L1-Akt-treated group compared to IV-UMSC-PD-L1-Akt, IA-UMSC-PD-L1-Akt and control group (FIG. 9A). The IV-IA-UMSC-PD-L1-Akt-treated group showed significantly fewer CD68⁺ cells infiltration at the peri-infarct area at 3 days after MI than IV-UMSC-PD-L1-Akt, IA-UMSC-PD-L1-Akt and control group (FIG. 9B).

Example 12 UMSC-PD-L1-Akt Treatment
Attenuated the MI-Induced Fibrosis

Figures 9C, 10:
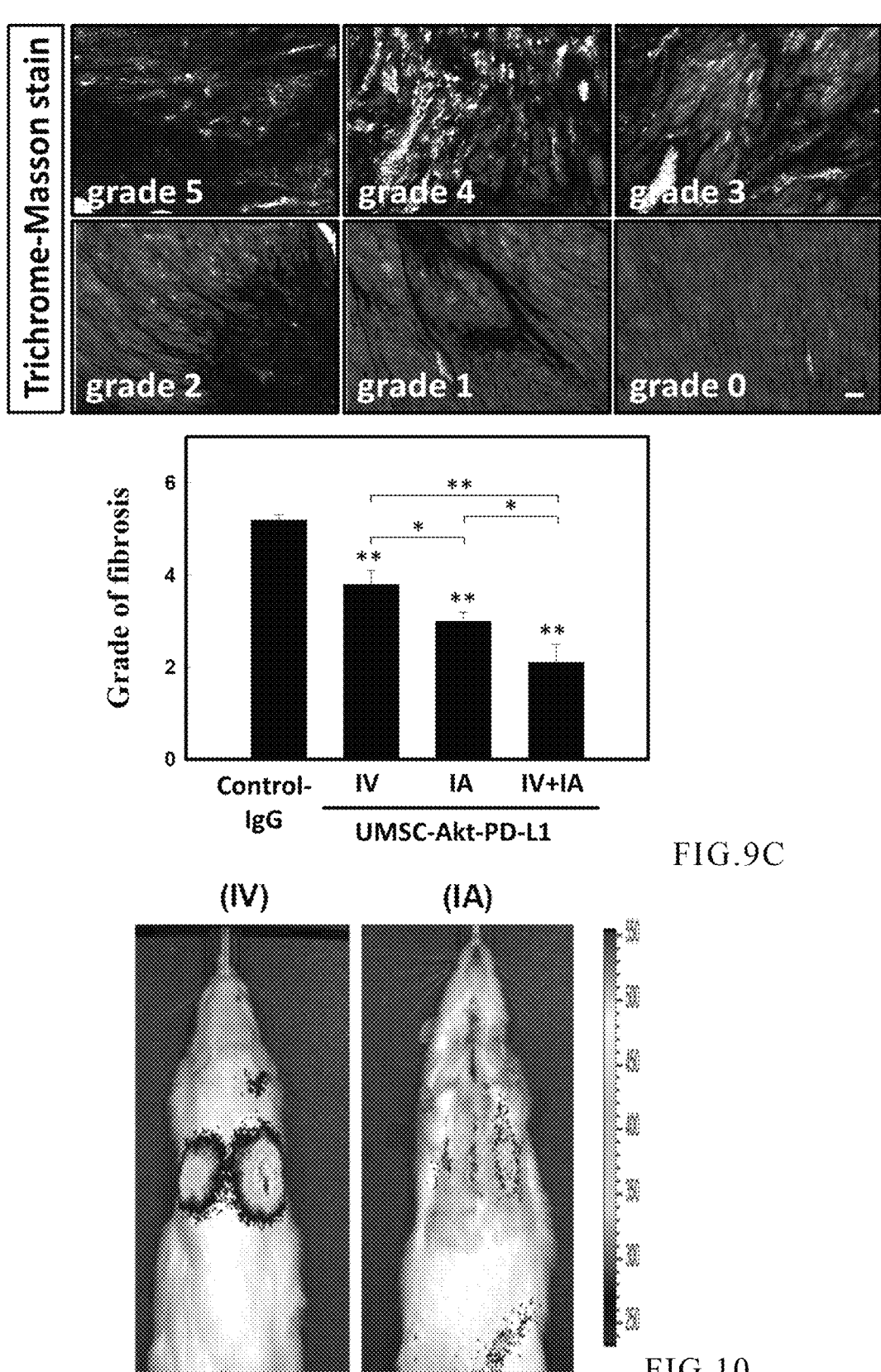
FIG. 9C shows the results of fibrosis of LV at 28 days post-MI in trichrome-stained in intravenous (IV), intracarotid (IA) and combined intravenous and intracarotid (IV+IA) injections of UMSC-PD-L1-Akt.
FIG. 10 shows the IVIS results of biodistribution at different time points after combined intravenous and intracarotid injections of UMSC-PD-L1-Akt-Luc.

Significantly increased fibrosis in the LV was observed at 28 days post-MI in trichrome-stained sections compared to sham (FIG. 3C). Interestingly, we observed significantly reduced fibrosis post-MI following IV-IA-UMSC-PD-L1-Akt treatment compared to IV-UMSC-PD-L1-Akt, IA-UMSC-PD-L1-Akt and control group (FIG. 9C).

Example 13 Targeting of UMSC-PD-L1-Akt-Luc in
the AMI Model

To demonstrate the UMSC-PD-L1-Akt homing effect, biodistribution of UMSC-PD-L1-Akt-Luc after intracarotid or intravenous implantation was performed using IVIS. Intravenous UMSC-PD-L1-Akt-Luc transplantation was initially entrapped in the lung capillary from 6 hours after injection, which showed an enhanced bioluminescent image of IVIS in the lung (FIG. 10). While in the intracarotid injection at 24 hours after MI, homing of UMSC-Akt-PD-L1-Luc did survive and relocate into the cardiac area without lung uptake from 6 hours to over one week (FIG. 10).

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

What is claimed is:

1. A population of genetically engineered mesenchymal stem cells (MSCs), wherein the MSCs are transfected with a hepatocyte growth factor (HGF) gene and a PD-L1 gene.

2. The population of genetically engineered MSCs of claim 1, wherein the MSCs are umbilical cord mesenchymal stem cells (UMSCs), adipose derived mesenchymal stem cells (ADSCs), or bone marrow mesenchymal stem cells (BMSCs).

3. The population of genetically engineered MSCs of claim 1, wherein the HGF gene and the PD-L1 gene are comprised in a vector.

4. The population of genetically engineered MSCs of claim 3, wherein the vector is a lentiviral vector.

5. A pharmaceutical composition comprising the population of genetically engineered MSCs of claim 1.

6. A method for making the population of genetically engineered MSCs of claim 1, comprising transfecting the MSCs with an HGF gene and a PD-L1.

7. The method of claim 6, wherein the MSCs are UMSCs, ADSCs or BMSCs.

8. A method for preventing, ameliorating and/or treating an ischemia condition, enhancing neuroregeneration or reducing neuronal death in a subject in need thereof, comprising administering an effective amount of the population of genetically engineered MSCs of claim 1 to the subject.

9. The method of claim 8, wherein the effective amount ranges from about $1 \times 10^5$ cells to about $1 \times 10^8$ cells.

10. The method of claim 8, wherein the administration reduces inflammatory response but enhances accumulation of CD8⁺CD122⁺ Tregs in an ischemic tissue.

11. The method of claim 10, wherein the ischemic tissue is an ischemic brain tissue.

12. The method of claim 8, wherein the administration increases the expression of regulatory molecules on T cells in the subject.

13. The method of claim 8, wherein the ischemia condition is a stroke.

14. The method of claim 8, wherein the ischemia condition is myocardial infarction (MI).

15. The method of claim 14, wherein the MI is acute myocardial infarction (AMI).

16. The method of claim 8, wherein the administration is intravenous injection, intracarotid injection, intraarterial injection, or a combination thereof.

17. The method of claim 8, wherein the administration is intracarotid injection in combination with intravenous injection or intraarterial injection in combination with intravenous injection in a subject suffering from a stroke or AMI.

18. The method of claim 17, wherein the administration is in an effective amount ranging from about $1 \times 10^4$ cells to about $1 \times 10^6$ cells for intracarotid injection and about $3 \times 10^4$ cells to about $1 \times 10^7$ cells for intravenous injection.

19. The method of claim 8, wherein the administration attenuates MI-Induced fibrosis, reduces inflammation on ischemic tissue, attenuates post-MI dysfunction and reduces infarct size after MI; increases the expression of regulatory molecules on T cells in spleens after a stroke; or reduces neuronal death from stroke brain damage.

*    *    *    *    *